United States Patent [19]

Heckel et al.

[11] Patent Number: 5,294,626
[45] Date of Patent: Mar. 15, 1994

[54] ARYLSULPHONAMIDES PHARMACEUTICAL COMPOSITIONS CONTAINING THESE COMPOUNDS

[75] Inventors: Armin Heckel, Biberach; Josef Nickl, deceased, late of Biberach, by Ema Nickl, heir; Rainer Soyka, Biberach; Wolfgang Eisert, Biberach; Thomas Muller, Biberach; Johannes Weisenberger, Biberach; Christopher Meade, Bingen-Buedesheim; Gojko Muacevic, Ingelheim am Rhein, all of Fed. Rep. of Germany

[73] Assignee: Dr. Karl Thomas GmbH, Biberach an der Riss, Fed. Rep. of Germany

[21] Appl. No.: 523,167

[22] Filed: May 14, 1990

[30] Foreign Application Priority Data

May 12, 1989 [DE] Fed. Rep. of Germany ....... 3915506
Sep. 28, 1989 [DE] Fed. Rep. of Germany ....... 3932403

[51] Int. Cl.⁵ .................... C07D 213/56; A61K 31/44
[52] U.S. Cl. .................................. 514/357; 514/336; 546/284; 546/333
[58] Field of Search ............... 546/284, 333; 514/336, 514/357

[56] References Cited

FOREIGN PATENT DOCUMENTS 098690 6/1983 European Pat. Off. ............ 546/269
135316 7/1984 European Pat. Off. ............ 546/269
287270 4/1988 European Pat. Off. ............ 546/304
304271 8/1988 European Pat. Off. ............ 549/29

*Primary Examiner*—C. Warren Ivy
*Assistant Examiner*—Zinna N. David
*Attorney, Agent, or Firm*—D. E. Frankhouser; M-E. M. Timbers; A. R. Stempel

[57] ABSTRACT

The invention relates to new arylsulphonamides of the formula

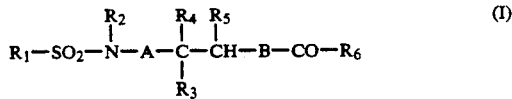

(wherein A, B and $R_1$ to $R_6$ are as defined in claim 1, the enantiomers, the cis- and trans-isomers thereof where $R_4$ and $R_5$ together represent a carbon-carbon bond, and the addition salts thereof, more particularly for pharmaceutical use the physiologically acceptable addition salts thereof with inorganic or organic bases, if $R_6$ represents a hydroxy group) which have useful pharmacological properties, particularly antithrombotic activities and thromboxane-mediating activities. Furthermore, the new compounds are also thromboxane antagonists (TRA) and thromboxane synthesis inhibitors (TSH) They also have an effect on $PGE_2$ production.

7 Claims, No Drawings

ARYLSULPHONAMIDES PHARMACEUTICAL COMPOSITIONS CONTAINING THESE COMPOUNDS

The present invention relates to new arylsulphonamides of the formula

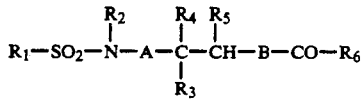
(I)

the enantiomers thereof, and cis- and trans-isomers if $R_4$ and $R_5$ together represent a carbon-carbon bond, and the addition salts thereof, more particularly for pharmaceutical use the physiologically acceptable salts of addition with organic or inorganic bases if $R_6$ represents a hydroxy group, which have valuable pharmacological properties, more particularly an antithrombotic activity. In addition, the new compounds are also thromboxane antagonists (TRA) and thromboxane synthesis inhibitors (TSH) and thus inhibit the activities which are mediated by thromboxane. Furthermore they affect the production of $PGE_2$ in the lungs and the production of $PGD_2$, $PGE_2$ and $PGF_{2\alpha}$ in human thrombocytes.

The present invention thus relates to the new compounds of formula I above, the salts of addition thereof with organic or inorganic bases, and particularly for pharmaceutical use the physiologically acceptable addition salts thereof, pharmaceutical compositions which contain these compounds and processes for preparing them.

In the above formula $R_1$ represents a phenylalkyl, trialkylphenyl, tetramethylphenyl or pentamethylphenyl group, a thienyl group optionally substituted by a halogen atom or an alkyl group, or a phenyl group which may be mono-substituted by a nitro group or mono- or disubstituted by a halogen atom or by an alkyl, trifluoromethyl or alkoxy group, the substituents being identical or different, $R_2$, $R_4$ and $R_5$, which may be identical or different, each represents a hydrogen atom or an alkyl group or $R_2$ represents a hydrogen atom or an alkyl group and $R_4$ and $R_5$ together represent a carbon-carbon bond, $R_3$ represents a pyridyl group optionally substituted by an alkyl group, $R_6$ represents a hydroxy, alkoxy, amino, alkylamino or dialkylamino group, A represents a group of formula

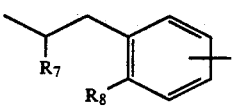

or

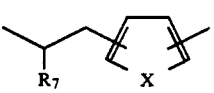

or

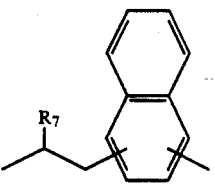

wherein $R_7$ represents a hydrogen atom or an alkyl group, $R_8$ represents a hydrogen atom or $R_7$ and $R_8$ together represent a methylene or ethylene group and X represents an alkyl-substituted imino group or an oxygen or sulphur atom, the —$CHR_7$— group being connected to the —$NR_2$— group, and B represents a carbon-carbon bond or a straight-chained $C_{1-4}$ alkylene group optionally substituted by one or two alkyl groups, whilst all the alkyl and alkoxy moieties mentioned hereinbefore may each contain 1 to 3 carbon atoms.

As examples of the definitions given for the groups hereinbefore:

$R_1$ may represent a benzyl, 2-phenylethyl, 3-phenylpropyl, 2,4,6-trimethylphenyl, 2,4,6-triethylphenyl, 2,4,6-tri-n-propylphenyl, 2,3,5,6-tetramethylphenyl, 3,4,5,6-tetramethylphenyl, 2,4,5,6-tetramethylphenyl, 2,3,4,5,6-pentamethylphenyl, 2-thienyl, 3-thienyl, 5-methyl-2-thienyl, 5-ethyl-2-thienyl, 5-n-propyl-2-thienyl, 5-n-isopropyl-2-thienyl, 5-chloro-2-thienyl, 5-bromo-2-thienyl, 5-methyl-3-thienyl, 5-ethyl-3-thienyl, 5-n-propyl-3-thienyl, 5-n-isopropyl-3-thienyl, 5-chloro-3-thienyl, 5-bromo-3-thienyl, phenyl, 2-methylphenyl, 3-methylphenyl, 4-methylphenyl, 2-ethylphenyl, 3-ethylphenyl, 4-ethylphenyl, 4-isopropylphenyl, 2-trifluoromethylphenyl, 3-trifluoromethylphenyl, 4-trifluoromethylphenyl, 2-methoxyphenyl, 3-methoxyphenyl, 4-methoxyphenyl, 2-ethoxyphenyl, 3-ethoxyphenyl, 4 -ethoxyphenyl, 4-n-propoxyphenyl, 4-isopropoxyphenyl, 2-fluorophenyl, 3-fluorophenyl, 4-fluorophenyl, 2-chlorophenyl, 3-chlorophenyl, 4-chlorophenyl, 2-bromophenyl, 4-bromophenyl, 2-nitrophenyl, 4-nitrophenyl, 3,4-dimethylphenyl, 3,4-dimethoxyphenyl, 2,4-difluorophenyl, 2,4-dichlorophenyl, 2,5-dichlorophenyl, 2,4-dibromophenyl, 2,4-ditrifluoromethylphenyl, 2-methoxy-5-chlorophenyl or 2-methyl-5-chlorophenyl group, $R_2$, $R_4$, $R_7$ and $R_8$ may each represent a hydrogen atom, a methyl, ethyl, n-propyl or isopropyl group, $R_6$ may represent a hydroxy, methoxy, ethoxy, n-propoxy, isopropoxy, amino, methylamino, ethylamino, isopropylamino, dimethylamino, diethylamino, diisopropylamino or methyl-ethylamino group, $R_3$ may represent a 2-pyridyl, 3-pyridyl, 4-pyridyl, 4-methyl-pyrid-2-yl, 2-methyl-pyrid-3-yl, 2-methyl-pyrid-4-yl or 6-isopropyl-pyrid-2-yl group, X may represent an oxygen or sulphur atom, or an N-methylimino, N-ethylimino or N-isopropylimino group and B may represent a methylene, ethylene, n-propylene, n-butylene, α-methyl-ethylene, α-methyl-n-propylene, α-ethyl-n-propylene, α-n-propyl-n-propylene, α,α-dimethyl-n-propylene, α,α-diethyl-n-propylene, β-methyl-n-propylene, -methyl-n-propylene, α-methyl-n-butylene or α,α-dimethyl-n-butylene group, where the position indices for the alkyl substituents define their position relative to the —CO— group.

However, the preferred compounds of formula I above are those wherein

R₁ represents a benzyl, thienyl, chlorothienyl, dichlorophenyl, dimethoxyphenyl, tetramethylphenyl or pentamethylphenyl group or a phenyl group optionally substituted by a fluorine or chlorine atom or by a nitro, methyl or trifluoromethyl group, R₂, R₄ and R₅ each represent a hydrogen atom or a methyl group or R₂ represents a hydrogen atom or a methyl group and R₄ and R₅ together represent a carbon-carbon bond, R₃ represents a pyridyl group, R₆ represents a hydroxy or methoxy group, A represents a group of formula

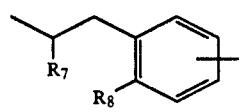

or

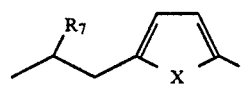

or

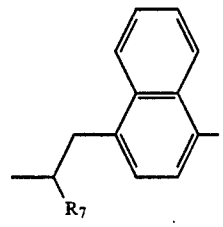

wherein

R₇ and R₈ each represent a hydrogen atom or together represent a methylene or ethylene group and X represents a sulphur atom or an N-methylimino group, —CHR₇— group being linked to the —NR₂— group, and B represents a carbon-carbon bond or a straight-chained C₂₋₄ alkylene group, the enantiomers, the cis and trans isomers where R₄ and R₅ together form a carbon-carbon bond, and the addition salts thereof, particularly for pharmaceutical use the physiologically acceptable salts of addition with organic or inorganic bases where R₆ represents a hydroxy group.

However, the particularly preferred compounds of formula I are those wherein

R₁ represents a tetramethylphenyl or pentamethylphenyl group or a phenyl group substituted in the 4-position by a methyl or trifluoromethyl group or by a fluorine, chlorine or bromine atom, R₂, R₄ and R₅ each represent a hydrogen atom or R₂ represents a hydrogen atom and R₄ and R₅ together represent a carbon-carbon bond, R₃ represents a 3-pyridyl group, A represents a group of the formula

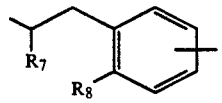

wherein

R₇ and R₈ each represent a hydrogen atom or

R₇ and R₈ together represent a methylene group, and

R₆ represents a hydroxy group, the enantiomers, the cis and trans isomers thereof where R₄ and R₅ together form a carbon-carbon bond, and the physiologically acceptable salts of addition with organic or inorganic bases.

According to the invention, the new compounds are obtained by the following methods:

a) acylation of a compound of formula

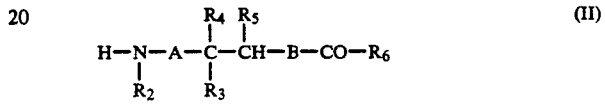

(wherein R₂ to R₆, A and B are as hereinbefore defined) with a sulphonic acid derivative of formula

wherein

R₁ is as hereinbefore defined and

X represents a nucleophilic leaving group such as a halogen atom or an alkoxy group, e.g. a chlorine or bromine atom or a methoxy or ethoxy group.

The reaction is preferably carried out in a solvent such as methanol, ethanol, water/methanol, dioxan, tetrahydrofuran or chloroform, optionally in the presence of an acid binding agent such as potassium carbonate, triethylamine or pyridine whilst the latter two may also be used as solvent, expediently at temperatures between 0° and 50° C., but preferably at ambient temperature.

b) In order to prepare compounds of formula I wherein R₆ represents a hydroxy group:

Cleaving a protecting group from a compound of general formula

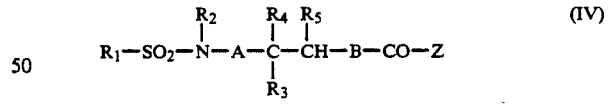

wherein

R₁ to R₅, A and B are as hereinbefore defined and Z represents a hydrolytically, thermolytically or hydrogenolytically removable protecting group for a carboxy group or a functional derivative of a carboxy group.

Examples of hydrolysable groups include functional derivatives of the carboxy group such as unsubstituted or substituted amides, esters, thioesters, orthoesters, iminoethers, amidines or anhydrides, the nitrile group, ether groups such as the methoxy, ethoxy, tert.butoxy or benzyloxy group or lactones and examples of thermolytically removable groups include for example esters with tertiary alcohols, e.g. the tert.butylester, and examples of hydrogenolytically removable groups include aralkyl groups such as the benzyl group.

The hydrolysis is conveniently carried out either in the presence of an acid such as hydrochloric, sulphuric, phosphoric or trichloroacetic acid or in the presence of a base such as sodium hydroxide or potassium hydroxide in a suitable solvent such as water, water/methanol, ethanol, water/ethanol, water/isopropanol or water/dioxan at temperatures of between −10° and 120° C., e.g. at temperatures between ambient temperature and the boiling temperature of the reaction mixture.

If for example a compound of formula IV contains a nitrile or aminocarbonyl group, these groups may be converted to the carboxy group, preferably using 100% phosphoric acid, at temperatures between 100° and 180° C., preferably at temperatures between 120° and 160° C., or with a nitrite, e.g. sodium nitrite, in the presence of an acid such as sulphuric acid, which is conveniently used as solvent at the same time, at temperatures of between 0° and 50° C.

If for example a compound of formula IV contains an acid amide group such as the diethylaminocarbonyl or piperidinocarbonyl group, this group may preferably be converted into the carboxy group, preferably hydrolytically in the presence of an acid such as hydrochloric, sulphuric, phosphoric or trichloroacetic acid or in the presence of a base such as sodium hydroxide or potassium hydroxide in a suitable solvent such as water, water/methanol, ethanol, water/ethanol, water/isopropanol or water/dioxan at temperatures of between −10° and 120° C., e.g. at temperatures between ambient temperature and the boiling temperature of the reaction mixture.

If for example a compound of formula IV contains the tert.butyloxycarbonyl group, the tert.butyl group may also be cleaved thermally, optionally in an inert solvent such as methylene chloride, chloroform, benzene, toluene, tetrahydrofuran or dioxan and preferably in the presence of a catalytic amount of an acid such as p-toluenesulphonic, sulphuric, phosphoric or polyphosphoric acid, preferably at the boiling temperature of the solvent used, e.g. at temperatures of between 40° and 100° C.

If for example a compound of formula IV contains the benzyloxy or benzyloxycarbonyl group, the benzyl group may also be cleaved by hydrogenolysis in the presence of a hydrogenation catalyst such as palladium/charcoal in a suitable solvent such as methanol, ethanol, methanol/water, ethanol/water, glacial acetic acid, ethyl acetate, dioxan or dimethylformamide, preferably at temperatures of between 0° and 50° C., e.g. at ambient temperature and under a hydrogen pressure of 1 to 5 bar. During the hydrogenolysis, a halogen-containing compound can simultaneously be dehalogenated and any double bond present may be hydrogenated.

c) In order to prepare compounds of formula I wherein $R_4$ and $R_5$ each represent a hydrogen atom:

Hydrogenation of a compound of formula

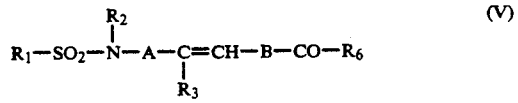

wherein $R_1$ to $R_3$, $R_6$, A and B are as hereinbefore defined.

The hydrogenation is carried out in a suitable solvent such as methanol, ethanol, dioxan, ethyl acetate or glacial acetic acid with catalytically activated hydrogen, e.g. with hydrogen in the presence of a hydrogenation catalyst such as Raney nickel, palladium, palladium/charcoal, platinum or platinum/charcoal and under a hydrogen pressure of 1 to 5 bar, or with nascent hydrogen, e.g. in the presence of iron/hydrochloric acid, zinc/glacial acetic acid, tin(II)chloride/hydrochloric acid or iron(II)sulphate/sulphuric acid, at temperatures of between 0° and 50° C., preferably at ambient temperature. However, the catalytic hydrogenation may also be carried out stereoselectively in the presence of a suitable catalyst.

Any nitro group which may be present in the group $R_1$ may be reduced at the same time, whilst any chlorine or bromine atom present in the group $R_1$ may be replaced by a hydrogen atom.

d) In order to prepare compounds of formula I wherein $R_4$ and $R_5$ together represent a carbon-carbon bond:

Reaction of a compound of formula

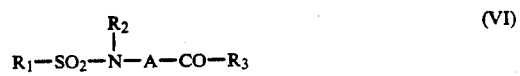

(wherein $R_1$ to $R_3$ and A are as hereinbefore defined) with a compound of formula

wherein

B and $R_6$ are defined as hereinbefore, $R_5'$ represents a hydrogen atom or a $C_{1-3}$ alkyl group and W represents a triphenylphosphonium halide, dialkylphosphonic acid or magnesium halide group, and optional subsequent dehydration.

The reaction is preferably carried out in a suitable solvent such as diethylether, tetrahydrofuran, dioxan or dimethylformamide at temperatures of between −30° and 100° C., preferably at temperatures of between −20° and 25° C.

However, it is particularly advantageous to carry out the reaction with a triphenylphosphonium halide of formula VII in the presence of a base such as potassium tert.butoxide or sodium hydride.

During the reaction with a magnesium halide of formula VII, in the case of the carbinol which is formed primarily in the reaction mixture, should the hydroxy group not be split off then this group is split off in the presence of an acid such as hydrochloric, sulphuric, phosphoric or trichloroacetic acid or in the presence of a base such as sodium hydroxide or potassium hydroxide in a suitable solvent such as ethanol, isopropanol or dioxan at temperatures of between 0° and 120° C., e.g. at temperatures between ambient temperature and the boiling temperature of the reaction mixture.

If according to the invention a compound of formula I is obtained wherein $R_2$ represents a hydrogen atom, this can be converted by alkylation into a corresponding compound of formula I wherein $R_2$ represents an alkyl group, or if a compound of formula I is obtained wherein $R_6$ represents or contains a hydroxy group, this can be converted by esterification or amidation into a corresponding compound of formula I wherein $R_6$ represents an alkoxy, amino, alkylamino or dialkylamino group.

The subsequent alkylation is preferably carried out in a solvent such as methylene chloride, tetrahydrofuran, dimethylformamide or dimethylsulphoxide in the presence of an alkylating agent such as methyl iodide, dimethylsulphate, ethyl bromide, n-propyl bromide or isopropyl bromide, optionally in the presence of an acid binding agent such as potassium carbonate at temperatures of between 0° and 70° C., preferably at temperatures between 20° and 50° C.

The subsequent esterification or amidation is conveniently carried out in a solvent, e.g. in an excess of the alcohol used, such as methanol, ethanol or isopropanol, or of the amine used such as ammonia, methylamine, n-propylamine or dimethylamine, in the presence of an acid activating agent such as thionyl chloride or hydrogen chloride gas at temperatures of between 0° and 180° C., but preferably at the boiling temperature of the reaction mixture.

The compounds of formula I obtained may, furthermore, be resolved into the enantiomers thereof. Thus, the compounds of formula I obtained which have only one optically active centre can be resolved into their optical antipodes using known methods (see Allinger N. L. and Eliel E. L. in "Topics in Stereochemistry", Vol. 6, Wiley Interscience, 1971), e.g. by recrystallisation from an optically active solvent or by reaction with an optically active substance which forms salts with the racemic compound, particularly bases, and separating the mixture of salts thus obtained, e.g. on the basis of their differing solubilities, into the diastereoisomeric salts from which the free antipodes can be released by the action of suitable agents. Optically active bases in common use include the D- and L-forms of α-phenylethylamine or cinchonidine.

Moreover, the compounds of formula I obtained which have at least 2 asymmetric carbon atoms can be resolved into their diastereoisomers on the basis of their physical-chemical differences using methods known per se. e.g. chromatography and/or fractional crystallisation. A pair of enantiomers obtained in this way can subsequently be resolved into the optical antipodes thereof as described above. If for example a compound of formula I contains two optically active carbon atoms, the corresponding (R R', S S') and (R S', S R') forms are obtained.

In addition, the compounds of formula I obtained wherein $R_4$ and $R_5$ together represent a carbon-carbon bond can be converted by conventional methods, e.g. by chromatography on a carrier such as silica gel, or by crystallisation, into their cis and trans isomers.

Furthermore, the new compounds of formula I thus obtained, if they contain a carboxy group, may if desired subsequently be converted into their salts of addition with organic or inorganic bases, and for pharmaceutical in particular use into the physiologically acceptable addition salts. Examples of such bases include sodium hydroxide, potassium hydroxide, cyclohexylamine, ethanolamine, diethanolamine and triethanolamine.

The compounds of formulae II to VII used as starting materials may be obtained by methods known from the literature or else are already known from the literature themselves.

A compound of formula II used as starting material is obtained from a corresponding N-acylamino compound by acylation according to Friedel-Craft, subsequent deacylation and, optionally, subsequent reduction, hydrolysis and/or esterification or by reaction of a corresponding magnesium or lithium compound with a correspondingly substituted pyridine compound such as 3-cyano-pyridine, pyridine-3-aldehyde or a pyridine-3-carboxylic acid derivative, optionally followed by oxidation.

The compounds of formulae IV, V and VI used as starting materials are obtained by reacting a corresponding amino compound with a corresponding sulphonyl halide.

The compounds of formula VII used as starting materials are obtained by reacting a corresponding halocarboxylic acid with triphenylphosphine or with a trialkylphosphonic ester.

As already mentioned hereinbefore, the new compounds and the physiologically acceptable addition salts thereof with organic or inorganic bases have valuable pharmacological properties, particularly antithrombotic effect and an inhibitory effect on blood platelet aggregation. They are also thromboxane antagonists and thromboxane synthesis inhibitors, whilst it is particularly worth noting that the compounds of formula I have this activity at the same time. They also have an effect on $PGE_2$ production in the lungs and on $PGD_2$, $PGE_2$ and $PGF_{2\alpha}$ production in human thrombocytes.

The following new compounds, for example:

A = 6-(2-(4-toluenesulphonylamino)indan-5-yl)-6-(3-pyridyl)hex-5-enoic acid,

B = 6-(4-(2-(4-chlorobenzenesulphonylamino)ethyl)-phenyl)-6-(3-pyridyl)hex-5-enoic acid, C = 6-(2-(4-chlorobenzenesulphonamino)indan-5-yl)-6-(3-pyridyl)hexanoic acid, D = 6-(4-(2-(4-chlorobenzenesulphonylamino)ethyl)-phenyl)-6-(3-pyridyl)hexanoic acid and E = 6-(4-(2-(4-trifluoromethylbenzenesulphonyl-amino)ethyl)phenyl)-6-(3-pyridyl)hex-5-enoic acid were tested for their biological properties as follows:

1. Antithrombotic activity

Method

The thrombocyte aggregation is measured using the Born and Cross method (J. Physiol. 170: 397 (1964)) in platelet-rich plasma taken from healthy volunteers. To inhibit coagulation the blood is mixed with 3.14% sodium citrate in a ratio by volume of 1:10.

Collagen-induced aggregation

The pattern of the decrease in optical density of the platelet suspension is photometrically measured and recorded after the addition of aggregation-triggering substance. The rate of aggregation is concluded from the angle of inclination of the density curve. The point on the curve where there is maximum light transmittance is used to calculate the optical density.

The amount of collagen used is as small as possible but sufficient to produce an irreversible reaction curve. Standard commercial collagen produced by Hormonchemie of Munich is used. Before the addition of the collagen the plasma is incubated for 10 minutes with the substance at 37° C.

From the measurements obtained an $EC_{50}$ is determined graphically, indicating a 50% change in the optical density in terms of the inhibition of aggregation.

The Table which follows contains the results found:

| Substance | $EC_{50}$ [μMol/l] |
| --- | --- |
| A | 0.3 |
| B | 0.15 |
| C | 0.3 |

-continued

| Substance | EC$_{50}$ [μMol/l] |
|---|---|
| D | 1.2 |
| E | 0.1 |

2. Thromboxane-antagonistic activity

Venous human blood is anti-coagulated with 13 mM Na$_3$ citrate and centrifuged for 10 minutes at 170×g. The supernatant platelet-rich plasma is passed through a Sepharose 2B column in order to remove the plasma proteins. Aliquots of the platelet suspension obtained are incubated with the test substance, the ligand ($^3$H-labelled) and a marker ($^{14}$C-labelled) for 60 minutes at ambient temperature and then centrifuged for 20 seconds at 10,000×g. The supernatant is removed and the pellet is dissolved in NaOH. The $^3$H activity in the supernatant corresponds to the free ligand, $^{14}$C gives the concentration of the marker. $^3$H in the pellet corresponds to the bound ligand whilst $^{14}$C is used to correct for the ligand in the extracellular space. After the process has been repeated, the displacement curve is determined from the binding values for different concentrations of the test substance and the IC$_{50}$ is determined.

| Substance | IC$_{50}$ [μMol/l] |
|---|---|
| A | 0.023 |
| B | 0.02 |
| C | 0.08 |
| D | 0.08 |
| E | 0.028 |

3. Determining the inhibitory effect on thromboxane synthetase

Venous human blood is anti-coagulated with 13 mM Na$_3$ citrate and centrifuged for 10 minutes at 170×g. The supernatant platelet-rich plasma is passed through a Sepharose 2B column in order to remove the plasma proteins. Aliquots of the platelet suspension obtained are incubated with the test substance or with a solvent as control for 10 minutes at ambient temperature and after the addition of $^{14}$C-labelled arachidonic acid incubation is continued for a further 10 minutes. After this has been stopped with 50 μl of citric acid, extraction is carried out 3×with 500 μl of ethyl acetate and the combined extracts are distilled off with nitrogen. The residue is taken up in ethyl acetate, placed on TLC film and separated with chloroform:methanol:glacial acetic acid:water (90:8:1:0.8, v/v/v/v). The dried TLC films are placed on X-ray film for 3 days, the autoradiograms were developed and the active zones were marked on the film using the autoradiograms. After cutting out, the activity is measured in a scintillation counter and the inhibition of the formation of TXB2 is calculated. The IC$_{50}$ is determined by linear interpolation.

| Substance | IC$_{50}$ [μMol/l] |
|---|---|
| A | 0.003 |
| B | 0.0008 |
| C | 0.003 |
| D | 0.001 |
| E | 0.006 |

4. Inhibition of bronchospasm induced by U-46619

Guinea-pigs anaesthetised with ethyl urethane and ventilated artificially under pressure limitation were repeatedly given intravenous injections of the thromboxane mimetic U-46619 (=[1R-[1α,4α,5β(Z),6α(1E, 3S*)]]-7-[6-(3-hydroxy-1-octenyl)-2-oxabicyclo[2.2.1-]hept-5-yl]-5-heptenoic acid). The bronchospasms produced were recorded plethysmographically according to a modification of the method of Konzett and Rössler (Konzett H. and Rössler R., Arch. exp. Pathol. u. Pharmakol. 195: 71–74 (1940)). The dosage of U-46619 selected (2.5–25 μg/kg i.v.) reduces the tidal volume by 60% or more. 10 minutes before the thromboxane mimetic is given, increasing doses of the substances to be tested are injected repeatedly by intraveous route. The percentage inhibition of the reduction in tidal volume is measured by comparison of the activity of U-46619 before and after different doses of the test substances. The Table which follows contains the ED$_{50}$ values found, which were determined by graphical extrapolation:

| Substance | ED$_{50}$ [μg/kg] |
|---|---|
| A | 30 |
| B | 29 |

5. Inhibition of the lethal effects of endotoxin

Male Sprague-Dawley rate are primed by intravenous injection with 0.1 mg/kg of endotoxin (a lipopolysaccharide from E. coli 0111:B4) one week before the main study. In the main study, a potentially lethal dose of E. coli (40 mg/kg) is injected intravenously and the subsequent mortality recorded over an observation period of seven days.

The test animals are given test substance B as a suspension in 0.5% tylose by oral route one hour before and 4, 8, 24 and 48 hours after the second injection of endotoxin. The following Table contains the values found:

| Amount of Substance B administered at each dosage time point (mg/kg) | Rats alive/total | |
|---|---|---|
| | after 2 days | after 7 days |
| 0 | 2/10 | 2/10 |
| 1 | 7/10 | 6/10 |
| 10 | 8/10 | 5/10 |

6. Inhibition of bronchospasm induced by arachidonic acid

Guinea-pigs anaesthetised with ethyl urethane and ventilated artificially under pressure limitation are intravenously injected with arachidonic acid (a thromboxane precursor) and the consequent bronchospasms are recorded using a modified form of the method of Konzett and Rössler. The doses of arachidonic acid (0.5–2.0 mg/kg) are selected so as to give a 60% reduction in tidal volume. Increasing doses of test substance B are injected 10 minutes before the arachidonic acid. The percentage inhibition of reduction in tidal volume is determined by comparison of the maximum reduction after the administration of arachidonic acid and the corresponding value after pretreatment with the test substance. The ED$_{50}$ value for substance B, determined by graphical extrapolation, was 8.1 μg/kg.

7. Inhibition of antigen-induced anaphylaxis

Male guinea-pigs are sensitised to ovalbumin by the administration of 40 mg/kg of ovalbumin, adsorbed onto an aluminium hydroxide adjuvant, by intraperitoneal route. Approximately 6 weeks later they are given a subcutaneous injection of 0.1 mg/kg of mepyramine hydrochloride in order to reduce the histamine component of the anaphylactic response, which is otherwise very marked in guinea-pigs. 30 minutes later the animals are exposed for 90 seconds to nebulised 0.9% saline solution containing 3% ovalbumin. 10 minutes after the start of inhalation, the animals are killed by a blow to the neck and the lungs are rapidly removed. Their volume, the so-called relaxation volume, is measured. The consequences of anaphylaxis or bronchoconstriction are associated with an increase in the relaxation volume (see Drazen I. M. and Austen K. F. in J. Appl. Physiol. 39, 916–919 (1975)).

The following Table contains the values found:

| Animals | Mean lung relaxation volume (ml) | |
|---|---|---|
| | First study | Second study |
| Guinea-pigs exposed to aerosol without test substance | 7.52 (n = 6) | 7.51 (n = 6) |
| Guinea-pigs 60 minutes before inhalation pretreated with 2.5 mg/kg of substance B by oral route | 4.34 (n = 6) | 3.81 (n = 6) |

Unsensitised animals exposed to the ovalbumin or sensitised animals exposed to a control aerosol (saline solution) showed a relaxation volume of 1.5 ml or less in every case.

8. Effect on production of thromboxane and $PGE_2$ in an isolated lung

Guinea-pigs are killed by a blow to the neck, the lungs are rapidly removed and washed with a tyrode solution through the pulmonary artery. The lung is perfused with the same solution (0.5 ml/min.) and ventilated under negative pressure (frequency: 52 breaths per minute, maximum pressure $-20$ cm $H_2O$). A 0.1 ml bolus of bradykinin (0.2 $\mu M$) is injected via the pulmonary arteria on two occasions, with approximately 60 minutes between boli. From 30 minutes before the second bradykinin injection 1$\mu M$ of substance B is continually added to the lung perfusate. The control lungs are perfused without the added substance. The perfusate is collected for 2 minutes before the administration of bradykinin and 10 minutes thereafter. The samples are left to stand for 20 minutes at ambient temperature (conversion of thromboxane $A_2$ into $B_2$) and are then frozen at $-20°$ C.

The concentrations of thromboxane $B_2$ and $PGE_2$ are determined by radioimmunoassay. The results which follow show that 1 $\mu M$ of substance B in the lung perfusate hinders thromboxane production whilst promoting the formation of $PGE_2$:

| Substance present in perfusate time of 2nd administration of bradykinin | Ratio of mediator release | | | | | |
|---|---|---|---|---|---|---|
| | Thromboxane $B_2$ | | | After 2nd administration of bradykinin After 1st administration of bradykinin $PGE_2$ | | |
| 1 $\mu M$ B | 0.0 | 0.0 | | 5.08 | 2.23 | |
| control | 1.18 | 0.50 | 0.84 | 1.28 | 1.12 | 1.09 |

9. Acute toxicity

The acute toxicity of the test substances was determined as a guide on groups of 10 mice after oral administration of a single dose (observation period: 14 days):

| Substance | Approximate acute toxicity |
|---|---|
| A | 250 mg/kg (0 out of 10 animals died) |
| B | 250 mg/kg (0 out of 10 animals died) |
| C | 250 mg/kg (0 out of 10 animals died) |
| D | 250 mg/kg (0 out of 10 animals died) |
| E | 250 mg/kg (0 out of 10 animals died) |

In view of their pharmacological properties the new compounds and the physiologically acceptable addition salts thereof are suitable for the treatment and prevention of thromboembolic disorders such as coronary infarct, cerebral infarct, so-called transient ischaemic attacks, amaurosis fugax and for the prevention of arteriosclerosis and metastasis and for treating ischaemia, asthma and allergies.

The new compounds and the physiologically acceptable addition salts thereof are also useful in the treatment of diseases in which thromboxane-mediated constriction or $PGE_2$-mediated dilation of the capillaries are involved, e.g. in pulmonary hypertension. They may also be used to reduce the severity of transplant rejection, to decrease the renal toxicity of substances such as cyclosporin, for the treatment of kidney diseases, particularly for the treatment or prevention of changes in the kidneys in connection with hypertension, systemic lupus or obstruction of the ureter and in shock states associated with septicaemia, trauma or burns.

The dose required to achieve such an effect is expediently 0.3 to 4 mg/kg of body weight, preferably 0.3 to 2 mg/kg of body weight, two to four times a day. For this purpose, the compounds of formula I according to the invention, optionally combined with other active substances, may be made into conventional galenic preparations such as tablets, coated tablets, capsules, powders, suspensions or suppositories, by the use of one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetyl stearyl alcohol, carboxymethylcellulose or fatty substances such as hard fat or suitable mixtures thereof.

The present invention also relates to new pharmaceutical compositions containing a compound of formula I prepared according to the invention together with a PDE inhibitor or a lysing agent.

Examples of PDE inhibitors include:

2,6-bis(diethanolamino)-4,8-dipiperidino-pyrimido-[5,4-d]pyrimidine (dipyridamole), 2,6-bis(diethanolamino)-4-piperidino-pyrimido[5,4-d]pyrimidine (mopidamole), 2-(4-methoxy-phenyl)5(6)-(5-methyl-3-oxo-4,5-dihydro-2H-6-pyridazinyl)-benzimidazole (pimobendan), 2-(4-hydroxy-phenyl)-5(6)-(5-methyl-3-oxo-4,5-dihydro-2H-6-pyridazinyl)-benzimidazole, 1-(1-oxido-thiomorpholino)-3-piperazino-5-methylisoquinoline, 6-[4-(3,4-dichlorophenylsulphinyl)-butoxy]-3,4-dihydro-2-hydroxy-quinoline and 6-[4-(2-pyridylsulphonyl)-butoxy]-2-hydroxy-quinoline, the oral daily dose being 2.5 to 7.5 mg/kg, preferably 5 mg/kg, for dipyridamole, 15 to 25 mg/kg, preferably 20 mg/kg, for mopidamole, 0.05 to 0.15 mg/kg, preferably 0.08 to 0.10 mg/kg for 2-(4-methoxy-phenyl)-5(6)-(5-methyl-3-oxo-4,5-dihydro-2H-6-pyridazinyl)-benzimidazole, 0.05 to 0.15 mg/kg, preferably 0.08 to 0.10 mg/kg, for 2-(4-hydroxy-phenyl)-5(6)-(5-methyl-3-oxo-4,5-dihydro-2H-6-pyridazinyl)-benzimidazole, 0.20 to 2.00 mg/kg, preferably 0.40 to 1.00 mg/kg, for 1-(1-oxido-thiomorpholino)-3-piperazino-5-methylisoquinoline, 0.10 to 1.00 mg/kg, preferably 0.20 to 0.50 mg/kg, for 6-[4-(3,4-dichlorophenylsulphinyl)-butoxy]-3,4-dihydro-2-hydroxy-quinoline, and 0.10 to 1.00 mg/kg, preferably 0.20 to 0.50 mg/kg, for 6-[4-(2-pyridylsulphonyl)-butoxy]-2-hydroxy-quinoline, whilst suitable lysing agents are plasminogen activators such as t-PA, rt-PA, streptokinase, eminase or urokinase, the lysing agent being administered by parenteral route, preferably intravenously, e.g. t-PA or rt-PA in a dose of between 15 and 100 mg per patient, urokinase in a dose of between 250,000 and 3,000,000 units per patient, eminase in a dose of about 30 mg per patient and streptokinase in a dose of between $5 \times 10^4$ and $3 \times 10^7$ IU within 5 minutes and 24 hours.

For pharmaceutical use, a new combination containing 1 to 500 mg of a PDE inhibitor, but preferably 2 to 75 mg, plus 10 to 300 mg of a compound of formula I prepared according to the invention, but preferably 10 to 200 mg thereof, as well as the physiologically acceptable addition salts thereof together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetyl stearyl alcohol, carboxymethyl cellulose or fatty substances such as hard fat or suitable mixtures thereof may be formulated to produce conventional galenic preparations such as plain or coated tablets, capsules, powders, suspensions or suppositories. In order to achieve the desired results the preparation will be administered to adults 2 to 4 times a day, but preferably 3 to 4 times a day.

Furthermore, for pharmaceutical use, a new combination containing a lysing agent in the dosages given hereinbefore plus 10 to 300 mg of a compound of formula I prepared according to the invention, preferably 10 to 200 mg thereof, and the physiologically acceptable addition salts thereof may be incorporated in the usual parenteral, preferably the usual intravenous, preparations such as ampoules or infusions, and the preparation can be administered within 5 minutes and 24 hours.

Naturally, the individual active substances in the above-mentioned combinations may be administered if desired.

The Examples which follow are intended to illustrate the invention. In such examples, all "parts" are by weight and the eluant ratios are by volume.

EXAMPLE 1

6-(4-(2-(4-Chlorobenzenesulphonylamino)ethyl)-phenyl)-6-(3-pyridyl)hex-5-enoic acid a) 2-(p-Chlorobenzenesulphonylamino)ethyl-benzene To a mixture of 150 ml of ethylene chloride and 150 ml of water are added 30.3 g of 2-phenylethylamine, 12 g of sodium hydroxide and 0.5 g of tetrabutylammonium bromide. 65.5 g of 4-chlorobenzenesulphonic acid chloride are added to the mixture in batches with stirring. After 30 minutes the organic phase is separated off, evaporated down and the residue is recrystallised from toluene.

Yield: 65 g (88% of theory).
Melting point: 90° C.

b)
4-(2-(4-Chlorobenzenesulphonylamino)ethyl)phenyl-3-pyridyl ketone 100 g of aluminium trichloride are slowly combined with 25.5 ml of dimethylformamide in such a way that the temperature does not exceed 70° C. To this mixture are added 35.6 g of nicotinic acid chloride hydrochloride and 49 g of 2-(4-chlorobenzenesulphonylamino)ethyl benzene and it is heated to 100° C. for 2 hours. The reaction mixture is poured onto ice, neutralised and extracted with ethylene chloride. The organic phase is evaporated down and the residue is chromatographed over a silica gel column using ethylene chloride/ethanol (40:1).

Yield: 16.7 g (25% of theory).
Melting point: 150°–152° C.
$C_{20}H_{17}ClN_2O_3S$ (400.91): Calculated: C,59.92; H,4.28; N,6.99. Found: C,60.06 H,3.98; N,6.87.

c)
6-(4-(2-(4-Chlorobenzenesulphonylamino)ethyl)-phenyl)-6-(3-pyridyl)hex-5-enoic acid To a suspension of 6.7 g of 4-carboxybutyltriphenylphosphonium bromide and 4.5 g of potassium tert-.butoxide in 100 ml of tetrahydrofuran are added 4.0 g of 4-(2-(4-chlorobenzenesulphonylamino)ethyl)phenyl-3-pyridyl ketone at 0° C. and the mixture is stirred for 2 hours. The reaction mixture is decomposed with ice water and washed with toluene. The aqueous phase is acidified and extracted with ethylene chloride. The organic extract is concentrated by evaporation and the residue is chromatographed over a silica gel column with ethylene chloride/ethanol (20:1). The fraction which contains the product is evaporated down, the residue is dissolved in ethyl acetate and the cyclohexylammonium salt is precipitated by the addition of 2 ml of cyclohexylamine.

Yield: 1.9 g (36% of theory).
Melting point: 95° C. (decomp.).
$C_{25}H_{25}ClN_2O_4S \times 1/2$ cyclohexylamine (534.61): Calculated: C, 62.91; H,5.94; N,6.55. Found: C,62.80; H,6.03; N,6.72.

EXAMPLE 2

6-(1-(4-(2-(4-Chlorobenzenesulphonylamino)ethyl)-naphthyl))-6-(3-pyridyl)hex-5-enoic acid a)
1-(2-(p-Chlorobenzenesulphonylamino)ethyl)naphthalene Prepared from 1-(2-aminoethyl)naphthalene and 4-chlorobenzenesulphonic acid chloride analogously to Example 1a. The crude product was purified by column chromatography on silica gel using ethylene chloride/cyclohexane (2:1).

Yield: 92% of theory.
Melting point: 98°–99° C.
$C_{18}H_{16}ClNO_2S$ (345.87): Calculated: C,62.5; H,4.66; N,4.05. Found: C,62.39; H,4.68; N,3.86.

b)
4-(2-(4-Chlorobenzenesulphonylamino)ethyl)naphthyl-3-pyridyl ketone

Prepared from nicotinic acid chloride hydrochloride and 1-(2-(p-chlorobenzenesulphonylamino)ethyl)naphthalene analogously to Example 1b. The crude product was purified by column chromatography on silica gel using ethylene chloride/ethyl acetate (5:1).

Yield: 22% of theory.

Resin, $R_f$ value: 0.41 (silica gel: ethylene chloride/ethyl acetate=3:1), $C_{24}H_{19}ClN_2O_3S$ (450.96): Calculated: C,63.92; H,4.25; N,6.21. Found: C,63.54; H,4.43; N,6.01.

c)
6-(1-(4-(2-(4-Chlorobenzenesulphonylamino)ethyl)-naphthyl))-6-(3-pyridyl)hex-5-enoic acid Prepared from 4-(2-(4-chlorobenzenesulphonylamino)ethyl)-naphthyl-3-pyridyl ketone and 4-carboxybutyltriphenylphosphonium bromide analogously to Example 1c but without precipitation of a salt using cyclohexylamine.

Yield: 43% of theory,

Resin, $R_f$ value: 0.52 (silica gel: ethylene chloride/ethyl acetate=4:1)

$C_{29}H_{27}ClN_2O_4S$ (535.09): Calculated: C,65.10; H,5.09; N,5.24. Found: C,64.91; H,5.3; N,5.20.

EXAMPLE 3

6-(5-(2-(4-Fluorobenzenesulphonylamino)ethyl)-N-methylpyrrol-2-yl)-6- 3-pyridyl)hex-5-enoic acid a) 5-(2-(4-Fluorobenzenesulphonylamino)ethyl)-N-methylpyrrol-2-yl-3-pyridyl ketone A solution of 14.1 g of 2-(2-(4-fluorobenzenesulphonylamino)-ethyl)-N-methyl-pyrrole in 100 ml of toluene and 50 ml of dimethylformamide is combined with 9.8 g of nicotinic acid chloride hydrochloride, added in batches. The mixture is refluxed for 2 hours, poured onto ice, neutralised and extracted with ethylene chloride. The crude product is chromatographed over a silica gel column with ethylene chloride/ethanol (20:1).

Yield: 4.6 g (24% of theory),

Melting point: 140° C.

$C_{19}H_{18}FN_3O_3S$ (387.44) Calculated: C,58.90; H,4.68; N,10.85. Found: C,58.62; H,4.52; N,10.70.

b)
6-(5-(2-(4-Fluorobenzenesulphonylamino)ethyl)-N-methyl-pyrrol-2-yl)-6-(3-pyridyl)hex-5-enoic acid Prepared from 5-(2-(4-fluorobenzenesulphonylamino)ethyl)-N-methyl-pyrrol-2-yl-3-pyridyl ketone and 4-carboxybutyltriphenylphosphonium bromide analogously to Example 1c, but the crude product is purified by recrystallisation from water/isopropanol.

Yield: 55% of theory.

Melting point: 190° C.

$C_{24}H_{26}FN_3O_4S$ (471.56): Calculated: C,61.13; H,5.56; N,8.91. Found: C,61.23; H,5.72; N,9.00.

EXAMPLE 4

6-(5-(2-(4-Chlorobenzenesulphonylamino)ethyl)thiophen-2-yl)-6-(3-pyridyl)hex-5-enoic acid a)
2-(2-(p-Chlorobenzenesulohonylamino)ethyl)thiophene Prepared from 2-(2-aminoethyl)-thiophene and 4-chlorobenzenesulphonic acid chloride analogously to Example 1a.

Yield: 69% of theory.

Melting point: 93° C.

$C_{12}H_{12}ClNO_2S_2$ (301.83): Calculated: C,47.75; H,4.01; N,4.64. Found: C,47.75; H,3.88; N,4.45.

b)
5-(2-(4-Chlorobenzenesulphonylamino)ethyl)thiophen-2-yl-3-pyridyl ketone

A solution of 15 g of 2-(2-(4-chlorobenzenesulphonylamino)ethyl)-thiophene in 50 ml of ethylene chloride is added dropwise to a suspension of 20 g of aluminium trichloride and nicotinic acid chloride hydrochloride in 150 ml of ethylene chloride. The mixture is heated for 1½ hours to 50° C., then poured onto ice, the precipitate is suction filtered and recrystallised from methanol.

Yield: 3.7 g (17% of theory).

Melting point: 154°-160° C.

$C_{18}H_{15}ClN_2O_3S \times \frac{1}{2} HCl$ (433.06): Calculated: C,49.9; H,3.58; N;6.47.

Found: C,50.29; H,3.82; N;6.38.

c)
6-(5-(2-(4-Chlorobenzenesulphonylamino)ethyl)-thiopen-2-yl)-6-(3-pyridyl)hex-5-enoic acid Prepared from 5-(2-(4-chlorobenzenesulphonylamino)ethyl)thiophen-2-yl-3-pyridyl ketone and 4-carboxybutyltriphenylphosphonium bromide analogously to Example 1c, but after column chromatography the product is recrystallised from ethyl acetate.

Yield: 20% of theory,

Melting point: 138° C.

$C_{23}H_{23}ClN_2O_4S$ (491.04): Calculated: C,56.26; H,4.72; N,5.71. Found: C,56.24; H,4.67; N,5.70.

EXAMPLE 5

6-(2-(4-Chlorobenzenesulphonylamino)tetralin-6- and 7-yl)-6-(3-pyridyl)hex-5-enoic acid a) 2-Acetylaminotetralin-6- and 7-yl-3-pyridyl ketone Prepared from 2-acetylaminotetralin and nicotinic acid chloride analogously to Example 1b.

Yield: 35% of theory.

Resin, $R_f$ value: 0.28 (silica gel: ethylene chloride/ethanol=10:1)

$C_{18}H_{18}N_2O_2$ (294.40): Calculated: C,73.45; H,6.16; N, 9.52. Found: C,73.38; H, 6.23; N,9.26.

b) 2-(4-Chlorobenzenesulphonylamino)tetralin-6- and 7-yl-3-pyridyl ketone

The mixture of 2-acetylaminotetralin-6- and 7-yl-3-pyridyl ketone is refluxed for 20 hours in 150 ml of concentrated hydrochloric acid. The solvent is removed and the residue is treated with 4-chlorobenzenesulphonic acid chloride according to Example 1a.

Yield: 35% of theory.

Melting point: 152°–155° C. (ethyl acetate), $C_{22}H_{19}ClO_3S$ (426.94): Calculated: C,61.89; H,4.49; N,6.56, Found: C,61.92; H,4.45; N,61.46.

c) 6-(2-(4-Chlorobenzenesulphonylamino)tetralin-6- and 7-yl)-6-(3-pyridyl)hex-5-enoic acid Prepared from the mixture of 2-(4-chlorobenzenesulphonylamino)tetralin-6- and 7-yl-3-pyridyl ketone and 4-carboxybutyltriphenyl-phosphonium bromide analogously to Example 1c, but with no precipitation of a salt using cyclohexylamine.

Yield: 93% of theory.

Resin, $R_f$ value: 0.30 (silica gel: ethylene chloride/ethanol=10:1).

$C_{27}H_{27}ClN_2O_4S$ (511.07): Calculated: C,63.4; H,5.33; N,5.48. Found: C,63.29; H,5.31; N,5.22.

EXAMPLE 6

6-(5-(2-(4-Fluorobenzenesulphonylamino)ethyl)-N-methylpyrrol-2-yl)-6-(3-pyridyl)hexanoic acid A mixture of 2.36 g of 6-(5-(2-(4-fluorobenzenesulphonylamino)ethyl)-N-methyl-pyrrol-2-yl)-6-(3-pyridyl)hex-5-enoic acid, 0.4 g of sodium hydroxide and 1 g of 10% palladium/charcoal in 50 ml of methanol is hydrogenated under 5 bar of hydrogen pressure. Then the catalyst is filtered off, the filtrate is evaporated down, the residue is diluted with water, acidified and extracted with ethylene chloride. The organic extract is evaporated down and the residue recrystallised from ethyl acetate.

Yield: 2 g (85% of theory).

Melting point: 146°–149° C.

Calculated: C,60.88; H,5.96; N,8.87. Found: C,6.02; H,6.02; N,8.93.

EXAMPLE 7

6-(2-(4-Toluenesulphonylamino)indan-5-yl)-6-(3-pyridyl)hex-5-enoic acid

At 70° C., 42.7 g of nicotinic acid chloride hydrochloride are added in batches to 150 g of aluminium chloride and 31 ml of dimethylformamide. 35 g of 2-acetylaminoindane are added in batches to this mixture. After the mixture has been further heated at 80° C. it is cooled after 2 hours and the mixture is poured onto 200 g of ice and 100 ml of concentrated hydrochloric acid. The acidic solution is carefully neutralised with sodium hydroxide solution and then extracted 4× with 250 ml of chloroform. The organic phases are collected, dried over sodium sulphate and concentrated by rotary evaporation.

Yield: 43 g (76% of theory).

Melting point: 165°–167° C.

$C_{17}H_{16}N_2O_2$ (280.32): Calculated: C,72.8; H,5.75; N,9.99. Found: C,72.701 H,5.72; N,9.75.

b) 2-Aminoindan-5-yl-3-pyridyl ketone 51 g of 2-acetylamino-indan-5-yl-3-pyridyl ketone are refluxed for 16 hours with 250 ml of half concentrated hydrochloric acid. The solution is concentrated and then adjusted to pH 12 using 15N sodium hydroxide solution. The precipitate formed is washed with water and recrystallised from 100 ml of isopropanol.

Yield: 42 g (97% of theory),

Melting point: 205° C. (decomp.), $C_{15}H_{14}N_2O$ (238.29): Calculated: C,75.61; H,5.92; N,11.75. Found: C,75.44; H,6.04; N,11.85.

c) 2-(4-Toluenesulphonylamino)indan-5-yl-3-pyridyl ketone 21 g of 2-aminoindan-5-yl-3-pyridyl ketone are dissolved together with 18.9 g of p-toluenesulphonic acid chloride in 250 ml of methylene chloride. Then 9.2 g of triethylamine are added dropwise. After 4 hours the suspension is rotary-evaporated to dryness. The residue is suspended in water, made alkaline with sodium hydroxide solution and then suction filtered.

Yield: 30.4 g (88% of theory),

Melting point: 225°–228° C.

$C_{22}H_{20}N_2O_3S$ (392.47): Calculated: C,67.3; H,5.14; N,7.14. Found: C,67.12; H,5.16; N,6.95.

d) 6-(2-(4-Toluenesulphonylamino)indan-5-yl)-6-(3-pyridyl)hex-5-enoic acid 5 g of 2-(4-toluenesulphonylamino)indan-5-yl-3-pyridyl ketone are added to a suspension of 8 g of 4-carboxybutyl-triphenylphosphonium bromide and 5.6 g of potassium tert.butoxide in 100 ml of tetrahydrofuran under a nitrogen atmosphere. The suspension is stirred for a further 2 hours at 0° C., then added to water and washed with toluene. Then the aqueous phase is acidified with 3N formic acid and the precipitate formed is taken up in methylene chloride. The organic phase is dried over magnesium sulphate and rotary-evaporated. The oil obtained is chromatographed over a silica gel column using ethyl acetate as eluant.

Yield: 3.4 g (56% of theory),

Melting point: 150°–156° C.

$C_{27}H_{28}N_2O_4S$ (476.59): Calculated: C,68.04; H,5.92; N,5.88. Found: C,67.90; C,6.10; N,5.82.

EXAMPLE 8

Methyl 6-(2-(4-bromobenzenesulphonylamino)indan-5-yl)-6-(3-pyridyl)hex-5-enoate a) 6-(2-Acetylamino-indan-5-yl)-6-(3-pyridyl)hex-5-ene carboxylic acid 11.1 g of 4-carboxybutyltriphenylphosphonium bromide and 8.0 g of potassium tert.butoxide are placed in 100 ml of absolute tetrahydrofuran and stirred at 10° C. under a nitrogen atmosphere. Then 5.6 g of 2-acetylaminoindan-5-yl-3-pyridyl ketone are added in batches and stirred at ambient temperature for 2 hours. The reaction mixture is then poured onto ice water and washed with toluene. The aqueous phase is adjusted to pH 5 using 3N hydrochloric acid. The precipitate formed is taken up in methylene chloride, washed with water, dried over sodium sulphate and rotary evaporated. The product mixture is chromatographed over a silica gel column using ethyl acetate:ethanol:glacial acetic acid (94:5:1) as eluant.

Yield: 7.2 g (99% of theory),

Oil, $R_f$ value: 0.20 (silica gel: ethyl acetate/ethanol/glacial acetic acid=94:5:1).

b) Methyl 6-(2-aminoindan-5-yl)-6-(3-pyridyl)hex-5-enoate 3.1 g of 6-(2-acetylam:inoindan-5-yl)-6-(3-pyridyl)-hex-5-enoic acid are refluxed for 15 hours with 20 ml of half concentrated hydrochloric acid and then rotary evaporated. The residue is then added to 50 ml of methanol saturated with dry hydrogen chloride. After 30 minutes stirring at ambient temperature the reaction mixture is rotary evaporated to dryness. The residue is taken up in 1N sodium hydroxide solution and adjusted to pH 10. It is then extracted 3 times with 50 ml of methylene chloride, the organic phase is dried and rotary evaporated.

Yield: 2.45 g (50% of theory)

Resin, $R_f = 0.50$ (silica gel: toluene/dioxan/methanol/ammonia = 2:5:2:1)

$C_{21}H_{24}N_2O_2$ (336.44) Calculated: C,74.97; H,7.19; N,8.33. Found: C,75.00; H,7.01 N,8.11.

c) Methyl 6-(2-(4-bromobenzenesulphonylamino)indan-5-yl)-6-(3-pyridyl)hex-5-enoate 3.4 g of methyl 6-(2-aminoindan-5-yl)-6-(3-pyridyl)-hex-5-enoate is placed in 40 ml of chloroform together with 3.3 g of 4-bromobenzenesulphonic acid chloride and 1.8 g of triethylamine are added in batches at ambient temperature. After 30 minutes the solution is washed with water, dried and rotary evaporated. The yellow oil is then chromatographed over a silica gel column using cyclohexane/ethyl acetate (1:2).

Yield: 4.5 g (81% of theory).

Resin, $R_f$ value: 0.25 (silica gel: cyclohexane/ethyl acetate = 1:1).

$C_{27}H_{27}BrN_2O_4S$ (555.48): Calculated: C,58.38; H,4.90; N,5.04. Found: C,58.30; H,5.16; N,4.94.

The following compounds are obtained analogously:

methyl 6-(2-(4-chlorobenzenesulphonylamino)indan-5-yl)-6-(3-pyridyl)hex-5-enoate Resin, $R_f$ value: 0.32 (silica gel: cyclohexane/ethyl acetate = 1:1), $C_{27}H_{27}ClN_2O_4S$ (511.03): Calculated: C,63.46; H,5.32; N,5.48. Found: C,63.58; H,5.49; N,5.35.

methyl 6-(2-(4-fluorobenzenesulphonylamino)indan-5-yl)-6-(3-pyridyl)hex-5-enoate Resin, $R_f$ value: 0.82 (silica gel: toluene/dioxan/methanol/ammonia = 2:5:2:1).

$C_{27}H_{27}FN_2O_4S$ (494.58): Calculated: C,65.57; H,5.50; N,5.66. Found: C,65.39; H,5.78; N,5.48.

methyl 6-(2-(2-thiophenesulphonylamino)indan-5-yl)-6-(3-pyridyl)hex-5-enoate

Resin, $R_f$ value: 0.25 (silica gel: cyclohexane/ethyl acetate = 1:1), $C_{25}H_{26}N_2O_4S_2$ (482.61): Calculated: C,62.22; H,5.43; N,5.80. Found: C,62.28; H,5.60; N,5.53.

methyl 6-(2-(2,5-dichlorobenzenesulphonylamino)indan-5-yl)-6-(3-pyridyl)hex-5-enoate Resin, $R_f$ value: 0.38 (silica gel: cyclohexane/ethyl acetate = 1:1).

$C_{27}H_{26}Cl_2N_2O_4S$ (545.48): Calculated: C,59.45; H,4.80; N,5.14. Found: C,59.41; H,5.02; N,4.96.

methyl 6-(2-(4-nitrobenzenesulphonylamino)indan-5-yl)-6-(3-pyridyl)hex-5-enoate

Resin, $R_f$ value: 0.38 (silica gel: cyclohexane/ethyl acetate = 1:1), $C_{27}H_{27}N_3O_6S$ (521.59): Calculated: C,62.1; H,5.22; N,8.06. Found: C,62.22; H,5.45; N,7.90.

methyl 6-(2-(benzenesulphonylamino)indan-5-yl)-6-(3-pyridyl)hex-5-enoate

Resin, $R_f$ value: 0.20 (silica gel: cyclohexane/ethyl acetate = 1:1).

$C_{27}H_{28}N_2O_4S$ (476.59): Calculated: C,68.04; H,5.92; N,5.88. Found: C,67.98; H,6.07; N,5.60.

EXAMPLE 9

6-(2-(4-Bromobenzenesulphonylamino)indan-5-yl)-6-(3-pyridyl)hex-5-enoic acid 3.7 g of methyl 6-(2-(4-bromobenzenesulphonylamino)-indan-5-yl)-6-(3-pyridyl)hex-5-enoate are refluxed for 15 minutes in 30 ml of ethanol and with 1N of 15N sodium hydroxide solution. After cooling the solution is rotary evaporated and the residue is taken up in water and washed with 30 ml of methylene chloride.

Then the aqueous phase is adjusted to pH 4 using hydrochloric acid. The precipitate formed is washed and dried.

Yield: 3.2 g (88% of theory),

Melting point: 83°-102° C.

$C_{25}H_{26}BrN_2O_4S$ (541.46): Calculated: C, 57.68; H, 4.65; N, 5.17. Found: C, 57.58; H, 4.64; N, 4.99.

The following compounds are obtained analogously:

6-(2-(4-chlorobenzenesulphonylamino)indan-5-yl)-6-(3-pyridyl)hex-5-enoic acid

Melting point: 83°-98° C.

$C_{26}H_{25}ClN_2O_4S$ (497.01): Calculated: C, 62.83; H, 5.07; N, 5.64. Found: C, 62.64; H, 5.02; N, 5.57.

6-(2-(4-fluorobenzenesulphonylamino)indan-5-yl)-6-(3-pyridyl)hex-5-enoic acid

Melting point: 73°-90° C.

$C_{26}H_{25}FN_2O_4S$ (480.55). Calculated: C, 64.98; H, 5.24; N, 5.83. Found: C, 64.8; H, 5.23; N, 5.76.

6-(2-(2-thiophenesulphonylamino)indan-5-yl)-6-(3-pyridyl)hex-5-enoic acid

Melting point: 67°-90° C.

$C_{24}H_{24}N_2O_4S_2$ (468.58): Calculated: C, 61.52; H, 5.16; N, 5.98. Found: C, 61.38; H, 5.04; N, 5.70.

6-(2-benzenesulphonylamino)indan-5-yl)-6-(3-pyridyl)hex-5-enoic acid

Melting point: 70°-97° C.

$C_{26}H_{26}N_2O_4S$ (462.58); Calculated: C, 67.51; H, 5.67; N, 6.06. Found: C, 67.44; H, 5.8; N, 6.18.

6-(2-(4-nitrobenzenesulphonylamino)indan-5-yl)-6-(3-pyridyl)-hex-5-enoic acid

Melting point: 73°-92° C.

$C_{26}H_{25}N_3O_6S$ (507.56): Calculated: C, 61.53; 1 H, 4.96; N, 8.28. Found: C, 61.45; H, 5.0; N, 8.18.

6-(2-(2,5-dichlorobenzenesulphonylamino)indan-5-yl)-6-(3-pyridyl)hex-5-enoic acid Melting point: 79°-100° C.

$C_{26}H_{24}Cl_2N_2O_4S$ (531.45): Calculated: C, 58.76; H, 4.55; N, 5.27. Found: C, 58.78; H, 4.65; N, 5.11.

EXAMPLE 10

6-(4-(2-(4-Chlorobenzenesulphonylaminoethyl)phenyl-6-(3-pyridyl)-hexanoic acid a) 4-(2-Acetylaminoethyl)phenyl-3-pyridyl ketone 180 g of aluminium chloride are mixed with 35 ml of dimethylformamide and the temperature rises to 70° C. Then 66.8 g of nicotinic acid chloride hydrochloride are added, followed by 49 g of 2-acetylaminoethylbenzene at 70° C. After 2 hours the mixture is cooled and 60 ml of ethylene chloride are added. Then the mixture is poured onto ice water and 180 ml of concentrated hydrochloric acid. The aqueous phase is made alkaline with sodium hydroxide solution and then extracted with 3 times 100 ml of ethylene chloride. The organic phase is dried and rotary evaporated.

Yield: 70.4 g (87% of theory),

Oil, R$_f$ value: 0.47 (silica gel: ethylene chloride/methanol=9:1)

C$_{16}$H$_{16}$N$_2$O$_2$ (268.32): Calculated: C, 71.62; H, 6.01; N, 10.44. Found: C, 71.82; H, 6.20; N, 10.30.

b)
6-(4-(2-Acetylaminoethyl)phenyl)-6-(3-pyridyl)hex-5-enoic acid

Prepared analogously to Example 7d from 4-(2-acetylaminoethyl)-phenyl-3-pyridyl ketone and 4-carboxybutyl-triphenylphosphonium bromide.

Yield: 57% of theory,
Melting point: 80°–85° C.

C$_{21}$H$_{24}$N$_2$O$_3$ (352.4): Calculated: C, 71.5; H, 6.86; N, 7.95. Found: C, 71.23; H, 7.06; N, 7.94.

The following compounds are obtained analogously:
5-(4-(2-acetylaminoethyl)phenyl)-5-(3-pyridyl)pent-4-enoic acid Yield: 87% of theory,
Resin, R$_f$ value: 0.35 (silica gel: chloroform/methanol=10:1).

C$_{20}$H$_{22}$N$_2$O$_3$ (338.4): Calculated: C, 70.98; H, 6.55; N, 8.28. Found: C, 70.79; H, 6.39; N, 7.88.

7-(4-(2-acetylaminoethyl)phenyl)-7-(3-pyridyl)hept-6-enoic acid

Yield: 49% of theory,
Resin, R$_f$ value: 0.37 (silica gel: chloroform/methanol=10:1),
C$_{22}$H$_{26}$N$_2$O$_3$ (366.5): Calculated: C, 72.11; H, 7.15; N, 7.64. Found: C, 71.82; H, 7.4; N, 7.58.

c)
6-(4-(2-Acetylaminoethyl)phenyl-6-(3-pyridyl)-hexanoic acid 7.05 g of 6-(4-(2-acetylaminoethyl)phenyl)-6-(3-pyridyl)hex-5-enoic acid are dissolved in 85 ml of 0.7N sodium hydroxide solution and catalytically reduced at 40° C. with 1 g of palladium/charcoal. After the catalyst has been removed by suction filtering the residue is acidified to pH 6 and the oil precipitated is taken up in ethyl acetate and evaporated down. The crude product is recrystallised from methanol.

Yield: 4.7 g (66% of theory).
Melting point: 135°–139° C.

C$_{21}$H$_{26}$N$_2$O$_2$ (354.5): Calculated: C, 71.16; H, 7.39; N, 7.90. Found: C, 70.85; H, 7.50; N, 7.85.

The following compounds are obtained analogously:
5-(4-(2-acetylaminoethyl)phenyl)-5-(3-pyridyl)pentanoic acid Yield: 58% of theory.
Resin, R$_f$ value: 0.37 (silica gel: chloroform/methanol=10:1).

C$_{20}$H$_{24}$N$_2$O$_3$ (340.4): Calculated: C, 70.56; H, 7.11; N, 8.23. Found: C, 70.40; H, 6.97; N, 7.94.

7-(4-(2-acetylaminoethyl)phenyl)-7-(3-pyridyl)heptanoic acid

Yield: 98% of theory,
Resin, R$_f$ value: 0.43 (silica gel: chloroform/methanol=10:1).

C$_{22}$H$_{28}$N$_2$O$_3$ (368.5): Calculated: C, 71.71; H, 7.66; N, 7.60. Found: C, 71.58; H, 7.77; N, 7.22.

(d) 6-(4-(2-Aminoethyl)phenyl)-6-(3-pyridyl)hexanoic acid 4.0 g of 6-(4-(2-acetylaminoethyl)phenyl)-6-(3-pyridyl)hexanoic acid are refluxed for 18 hours with 50 ml of half concentrated hydrochloric acid. The mixture is then rotary evaporated and the residue is purified by chromatography over a column of silica gel using methanol.

Yield: 2.3 g (66% of theory), Resin, R$_f$ value: 0.27 (silica gel: methanol) C$_{19}$H$_{24}$N$_2$O$_2$ (312.4): Calculated: C, 73.05; H, 7.74; N, 8.97. Found: C, 72.81; H, 7.63; N, 8.83.

The following compounds are obtained analogously:
5-(4-(2-aminoethyl)phenyl)-5-(3-pyridyl)pentanoic acid Yield: 96% of theory.
Resin, R$_f$ value: 0.33 (silica gel: methanol).

C$_{18}$H$_{22}$N$_2$O$_2$$\times$0.5 HCl (317.1): Calculated: C, 68.17; H, 7.43; N, 9.39. Found: C, 68.27; H, 7.31; N, 8.99.

7-(4-(2-aminoethyl)phenyl)-7-(3-pyridyl)heptanoic acid

Yield: 96% of theory.
Resin, R$_f$ value: 0.59 (silica gel: methanol).

C$_{20}$H$_{26}$N$_2$O$_2$ (326.4): Calculated: C, 73.59; H, 8.03; N, 8.58. Found: C, 73.48; H, 8.00; N, 8.37.

e)
6-(4-(2-(4-Chlorobenzenesulphonylamino)ethyl)-phenyl)-6-(3-pyridyl)hexanoic acid 1.9 g of 6-(4-(2-aminoethyl)phenyl)-6-(3-pyridyl)-hexanoic acid are suspended in 150 ml of dioxan and 0 ml of 5% potassium carbonate solution are added thereto. 1.54 g of 4-chlorobenzenesulphonic acid chloride in 20 ml of dioxan are added to this mixture at ambient temperature. After 5 hours it is rotary evaporated to dryness, the residue is taken up in a little sodium hydroxide solution and then precipitated with dilute acetic acid. The precipitate is collected, dried and then chromatographed over a silica gel column using chloroform/methanol (10:1) as eluant.

Yield: 1.8 g (61% of theory).
Resin, R$_f$ value: 0.48 (silica gel: chloroform/methanol=10:1).

C$_{25}$H$_{27}$ClN$_2$O$_4$S (487.03): Calculated: C, 61.65; H, 5.59; N;5.79. Found: C, 61.59; H, 5.40; N, 5.74.

The following compounds are obtained analogously:
6-(4-(2-(4-fluorobenzenesulphonylamino)ethyl)-phenyl)-6-(3-pyridyl)hexanoic acid Yield: 11% of theory.
Resin, R$_f$ value: 0.53 (silica gel: chloroform/methanol=10:1), C$_{25}$H$_{27}$FN$_2$O$_4$S (470.60): Calculated: C, 63.81; H, 5.78; N, 5.95. Found: C, 63.75; H, 5.92; N, 5.80.

6-(4-(2-(4-toluenesulphonylamino)ethyl)phenyl)-6-(3-pyridyl)hexanoic acid

Yield: 13% of theory.
Resin, R$_f$ value: 0.55 (silica gel: chloroform/methanol=10:1).

C$_{26}$H$_{29}$N$_2$O$_4$S (466.60): Calculated: C, 66.93; H, 6.48; N, 6.00. Found: C, 66.81; H, 6.57; N, 5.94.

6-(4-(2-(4-bromobenzenesulphonylamino)ethyl)-phenyl)-6-(3-pyridyl)hexanoic acid

Yield: 24% of theory,
Resin, R$_f$ value: 0.34 (silica gel: chloroform/methanol=20:1).

C$_{25}$H$_{27}$BrN$_2$O$_4$S (531.50): Calculated: C, 56.50; H, 5.12; N, 5.27. Found: C, 56.41; H, 5.31; N, 5.17.

EXAMPLE 11

5-(4-(2-(4-Fluorobenzenesulphonylamino)ethyl)-phenyl)-5-(3-pyridyl)pentanoic acid Prepared analogously to Example 10e from 5-(4-(2-aminoethyl)phenyl)-5-(3-pyridyl)pentanoic acid and 4-fluorobenzenesulphonic acid chloride.

Yield: 28% of theory.

Resin, $R_f$ value: 0.33 (silica gel: chloroform/methanol=10:1),

Chd $24H_{25}FN_2O_4S$ (456.50): Calculated: C, 63.14;H, 5.52; N, 6.94. Found: C, 63.04; H, 5.60; N, 5.96.

EXAMPLE 12

5-(4-(2-(4-Chlorobenzenesulphonylamino)ethyl)-phenyl)-5-(3-pyridyl)pentanoic acid Prepared analogously to Example 10e from 5-(4-(2-aminoethyl)phenyl)-5-(3-pyridyl)pentanoic acid and 4-chlorobenzenesulphonic acid chloride.

Yield: 21% of theory.

Melting point: 70° C.

$C_{24}H_{25}ClN_2O_4S$ (473.00): Calculated: C, 60.94; H, 5.33; N, 5.92. Found: C, 61.01; H, 5.35; N, 5.70.

EXAMPLE 13

7-(4-(2-(4-Toluenebenzenesulphonylamino)ethyl)-phenyl)-7-(3-pyridyl)heptanoic acid Prepared analogously to Example 10e from 7-(4-(2-aminoethyl)phenyl)-7-(3-pyridyl)heptanoic acid and 4-toluenesulphonic acid chloride.

Yield: 78% of theory.

Resin, $R_f$ value: 0.42 (silica gel: chloroform/methanol=10:1), $C_{27}H_{32}N_2O_4S$ (480.60): Calculated: C, 67.47; H, 6.71; N, 5.83. Found: C, 67.34; H, 6.71; N, 5.74.

EXAMPLE 14

7-(4-(2-(4-Fluorobenzenesulphonylamino)ethyl)-phenyl)-7-(3-pyridyl)heptanoic acid Prepared analogously to Example 13 from 7-(4-(2-aminoethyl)phenyl)-7-(3-pyridyl)heptanoic acid and 4-fluorobenzenesulphonic acid chloride.

Yield: 66% of theory.

Resin, $R_f$ value: 0.20 (silica gel: chloroform/methanol=10:1).

$C_{26}H_{29}FN_2O_4S$ (484.6): Calculated: C, 64.44; H, 6.03; N, 5.72. Found: C, 64.48; H, 5.99; N, 5.72.

EXAMPLE 15

Methyl 5-(4-(2-(4-chlorobenzenesulphonylamino)ethyl)-phenyl)-5-(3-pyridyl)pentanoate 2.0 g of 5-(4-(2-(4-chlorobenzenesulphonylamino)ethyl)phenyl)-5-(3-pyridyl)pentanoic acid are dissolved in 30 ml of methanol and mixed with 3 ml of thionyl chloride at 0° C. The solution is stirred overnight, then rotary evaporated and the residue is chromatographed over a silica gel column.

Yield: 1.1 g (53% of theory).

Resin, $R_f$ value: 0.65 (silica gel: chloroform/methanol=95:5), $C_{26}H_{29}ClN_2O_4S$ (501.1): Calculated: C, 62.33; H, 5.83; N, 5.59. Found: C, 62.36; H, 6.01; N, 5.42.

EXAMPLE 16

Methyl 5-(2-(4-chlorobenzenesulphonylamino)indan-5-yl)-5-(3-pyridyl)-pent-4-enoate 3.7 g of 5-(2-(4-chlorobenzenesulphonylamino)indan-5-yl)-5-(3-pyridyl)pent-4-enoic acid are dissolved in 30 ml of methanol into which dry hydrogen chloride is introduced. The solution is stirred overnight and then rotary evaporated. Whilst cooling with ice, the base is liberated with aqueous potassium carbonate solution and then extracted with methylene chloride. The solution is rotary evaporated and the residue is chromatographed over a silica gel column.

Yield: 2.5 g (52% of theory).

Resin, $R_f$ value: 0.53 (silica gel: toluene/dioxan/ethanol/acetic acid=9:1:1:0.6).

$C_{26}H_{25}ClN_2O_4S$ (497.01); Calculated: C, 62.80; H, 5.1; N, 5.60., Found: C, 62.67; H, 5.39; N, 5.40.

The following compound is obtained analogously:

Methyl 7-(2-(4-chlorobenzenesulphonylamino)indan-5-yl)-7-(3-pyridyl)hept-6-enoate Yield: 73% of theory, Resin, $R_f$ value: 0.31 (silica gel: cyclohexane/ethyl acetate=1:1), $C_{28}H_{29}ClN_2O_4S$ (525.06): Calculated: C, 64.05; H, 5.56; N, 5.33. Found: C, 64.45; H, 6.15; N, 5.05.

EXAMPLE 17

5-(2-(4-Chlorobenzenesulphonylamino)indan-5-yl)-5-(3-pyridyl)pent-4-enoic acid

Prepared from methyl 5-(2-(4-chlorobenzenesulphonylamino)indan-5-yl)-5-(3-pyridyl)pent-4-enoate by hydrolysis with sodium hydroxide solution.

Yield: 95% of theory.

Melting point: 94°–114° C.

$C_{25}H_{23}ClN_2O_4S$ (482.98): Calculated: C, 62.20; H, 4.80; N, 5.80. Found: C, 62.14; H, 4.70; N, 5.81.

The following compound is obtained analogously:

7-(2-(4-chlorobenzenesulphonylamino)indan-5-yl)-7-(3-pyridyl)hept-6-enoic acid

Yield: 94% of theory.

Melting point: 66°–90° C.

$C_{27}H_{27}ClN_2O_4S$ (511.03): Calculated: C, 63.50; H, 5.30; N, 5.50. Found: C, 63.65; H, 5.29; N, 5.30.

EXAMPLE 18

(Z)- and (E)-6-(2-(4-Chlorobenzenesulphonylamino)indan-5-yl)-6-(3-pyridyl)hex-5-enoic acid 1.9 g of methyl 6-(2-(4-chlorobenzenesulphonylamino)-indan-5-yl)-6-(3-pyridyl)hex-5-enoate is chromatographed over a silica gel column using the eluant ethylene chloride/ethyl acetate/glacial acetic acid (70:30:5). The faster running substance is the Z isomer. The (Z) and (E) esters thus obtained are hydrolysed with sodium hydroxide solution according to Example 17.

(Z)-6-(2-(4-chlorobenzenesulphonylamino)indan-5-yl)-6-(3-pyridyl)-hex-5-enoic acid Yield: 200 mg (10% of theory).

Melting point: 70°–100° C.

$C_{26}H_{25}ClN_2O_4S$ (497.01): Calculated: C, 62.83; H, 5.07; N, 5.64. Found: C, 62.72; H, 5.24; N, 5.47.

(E)-6-(2-(4-chlorobenzenesulphonylamino)indan-5-yl)-6-(3-pyridyl)-hex-5-enoic acid Yield: 400 mg (20% of theory).
Melting point 75°–103° C.
$C_{26}H_{25}ClN_2O_4S$ (497.01): Calculated: C, 62.83; H, 5.07; N, 5.64. Found: C, 62.75; H, 5.14; N, 5.43.

EXAMPLE 19

6-(2-(4-Chlorobenzenesulphonylamino)indan-5-yl)-6-(3-pyridyl)hexanoic acid 3.0 g of 6-(2-(4-chlorobenzenesulphonylamino)indan-5-yl)-6-(3-pyridyl)hex-5-enoic acid are dissolved in 50 ml of 0.3N sodium hydroxide solution and hydrogenated with 1 g of palladium/charcoal at 40° C. and 3.5 bar for 12 hours. The catalyst is then removed by suction filtering and the filtrate is adjusted to pH 4 to 5. The product precipitated is separated off and taken up in chloroform. The organic extract is washed with water, dried and evaporated down. Then the mixture is chromatographed over a silica gel column using the eluant ethylene chloride/ethyl acetate/glacial acetic acid (70:30:2). The third fraction contains the desired product.

Yield: 0.4 g (13% of theory).
Melting point: 85°–100° C.
$C_{26}H_{27}ClN_2O_4S$: Calculated: C, 62.58; H, 5.45; N, 5.61. Found: C, 62.64; H, 5.45; N, 5.79.

EXAMPLE 20

7-(2-(4-Chlorobenzenesulphonylamino)indan-5-yl)-7-(3-pyridyl)heptanoic acid

Prepared analogously to Example 19 by reduction of 7-(2-(4-chlorobenzenesulphonylamino)indan-5-yl)-7-(3-pyridyl)hept-6-enoic acid with platinum/charcoal.

Yield: 40% of theory.
Resin, $R_f$ value: 0.3 (silica gel: ethylene chloride/ethyl acetate/acetic acid = 10:3:0.5).
$C_{26}H_{29}ClN_2O_4S$ (501.03):
Calculated: C, 62.32; H, 5.83; N, 5.59. Found: C, 62.56; H, 6.00; N, 5.32.

EXAMPLE 21

5-(2-(Benzenesulphonylamino)indan-5-yl)-5-(3-pyridyl)-pentanoic acid

Prepared from 5-(2-(4-chlorobenzenesulphonylamino)indan-5-yl)-5-(3-pyridyl)pent-4-enoic acid analogously to Example 19 by catalytic hydrogenation in the presence of platinum as catalyst.

Yield: 37% of theory.
Melting point: 80°–110° C.
Chd $25H_{25}ClN_2O_4S$ (485.00): Calculated: C, 61.91; H, 5.19; N, 5.77. Found: C, 61.85; H, 5.33; N, 6.05.

EXAMPLE 22

7-(2-(Benzenesulphonylamino)indan-5-yl)-7-(3-pyridyl)heptanoic acid

Prepared from 7-(2-(4-chlorobenzenesulphonylamino)indan-5-yl)-7-(3-pyridyl)hept-6-enoic acid by catalytic 1 hydrogenation analogously to Example 21.

Yield: 10% of theory.
Melting point: 60°–75° C.
$C_{27}H_{29}ClN_2O_4S$ (513.05): Calculated: C, 63.21; H, 5.69; N, 5.46. Found: C, 63.43; H, 5.88; N, 5.63.

EXAMPLE 23

3-(2-(4-Toluenesulphonylamino)indan-5-yl)-3-(3-pyridyl)-prop-2-enoic acid a) Ethyl 3-(2-(4-toluenesulphonylamino)indan-5-yl)-3-(3-pyridyl)prop-2-enoate At 5° C., 9.84 g of triethylphosphonoacetate are added to a suspension of 9.6 g of potassium tert.butoxide in 100 ml of tetrahydrofuran and 25 ml of dimethylformamide. After 30 minutes stirring at 0° C., 15.5 g of 2-(4-toluenesulphonylamino)indan-5-yl-3-pyridyl ketone are added. The mixture is then refluxed for 5 hours. The solution is poured onto ice water and extracted 4 times with 50 ml of methylene chloride. It is then dried, rotary evaporated and the residue is chromatographed over a silica gel column using ethylene chloride/ethyl acetate 9:1 as eluant.

Yield: 17.2 g (93% of theory).
$R_f$ value: 0.46/0.35 (silica gel: ethylene chloride/ethyl acetate = 1:1).

b) 3-(2-(4-Toluenesulphonylamino)indan-5-yl)-3-(3-pyridyl)-prop-2-enoic acid 4.2 g of ethyl 3-(2-(4-toluenesulphonylamino)indan-5-yl)-3-(3-pyridyl)-prop-2-enoate are refluxed for 30 minutes in 40 ml of ethanol and 1.5 ml of 15N sodium hydroxide solution. Then the cooled solution is washed 3 times with 50 ml of methylene chloride and then acidified. The precipitate formed is washed, dried and then recrystallised from n-butanol.

Yield: 2.3 g (58% of theory).
Melting point: 228°–230° C.
$C_{23}H_{22}N_2O_4S$ (422.5). Calculated: C, 65.38; H, 5.24; N, 6.63. Found: C, 65.32; H, 5.17; N, 6.48.

EXAMPLE 24

4-(2-(4-Toluenesulphonylamino)indan-5-yl)-3-(3-pyridyl)propanoic acid

Prepared analogously to Example 19 from 3-(2-(4-toluenesulphonylamino)indan-5-yl)-3-(3-pyridyl)prop-2-enoate and subsequent precipitation from dioxan by the addition of diisopropylether.

Yield: 74% of theory.
Melting point: 85°–97° C.
$C_{23}H_{22}N_2O_4S \times 0.8$ dioxan (424.51): Calculated: C, 63.57; H, 6.19; N, 5.66. Found: C, 63.39; H, 6.30; N, 5.62.

EXAMPLE 25

6-(4-(2-(4-Fluorobenzenesulphonylamino)ethyl)-phenyl)-6-(3-pyridyl)-hex-5-enoic acid 3.1 g of 6-(4-(2-aminoethyl)phenyl)-6-(3-pyridyl)hex-5-enoic acid (prepared analogously to Example 10d) are stirred into 150 ml of dioxan with 5 ml of saturated potassium carbonate solution. Then 2.9 g of 4-fluorobenzenesulphonic acid chloride in 20 ml of dioxan are added and the resulting mixture is stirred overnight at ambient temperature. Acetic acid is added and a precipitate is formed. This is separated off and taken up in ethyl acetate, then dried and evaporated down. Finally, the residue is chromatographed over a silica gel column using chloroform/methanol 20:1 as eluant.

Yield: 0.5 g (10% of theory).
Resin, $R_f$ value: 0.55 (silica gel: chloroform/methanol = 10:1).

$C_{25}H_{25}FN_2O_4S$ (470.6): Calculated: C, 64.09; H, 5.38; N, 5.98. Found: C, 63.77; H, 5.59; N, 6.00.

The following compounds are obtained analogously:

6-(4-(2-(4-toluenesulphonylamino)ethyl)phenyl)-6-(3-pyridyl)hex-5-enoic acid

Yield: 13% of theory.

Resin, $R_f$ value: 0.5 (silica gel: chloroform/methanol=10:1).

Chd $_{26}H_{28}N_2O_4S$ (464.6): Calculated: C, 67.22; H, 6.07; N, 6.03. Found: C, 67.06; H, 6.21; N, 5.86.

6-(4-(2-(4-bromobenzenesulphonylamino)ethyl)-phenyl)-6-(3-pyridyl)-hex-5-enoic acid Yield: 20% of theory.

Resin, $R_f$ value: 0.4 (silica gel: chloroform/methanol=10:1).

$C_{25}H_{25}BrN_2O_4S$ (529.5): Calculated: C, 56.71; H, 4.76; N, 5.29. Found: C, 56.72; H, 4.58; N, 5.12.

EXAMPLE 26

7-(4-(2-(4-Chlorobenzenesulphonylamino)ethyl)-phenyl)-7-(3-pyridyl)-hept-6-enoic acid Prepared from 4-(2-(4-chlorobenzenesulphonylamino)ethyl)phenyl-3-pyridyl ketone analogously to Example 7d.

Yield: 83% of theory,

Resin, $R_f$ value: 0.5 (silica gel: ethylene chloride/methanol=5:1).

$C_{26}H_{27}ClN_2O_4S$ (499.02): Calculated: C, 62.58; H, 5.45; N, 5.62. Found: C, 62.48; H, 5.40; N, 5.62.

EXAMPLE 27

6-(4-(2-(4-Chlorobenzenesulphonylamino)ethyl)-phenyl)-6-(3-pyridyl)-hex-5-enoic acid diethylamide 1.0 g of 6-(4-(2-(4-chlorobenzenesulphonylamino)ethyl)phenyl)-6-(3-pyridyl)hex-5-enoic acid are dissolved in 15 ml of tetrahydrofuran and stirred for 15 minutes with 0.49 g of carbonyldiimidazole. Then 1 ml of diethylamine is added and the mixture is refluxed for 2 hours. It is then concentrated by evaporation and the residue is taken up in ethyl acetate and dried. Finally, it is chromatographed over a silica gel column using ethyl acetate as eluant.

Yield: 0.6 g (54% of theory).

Oil, $R_f$ value: 0.23 (silica gel: ethyl acetate).

$C_{29}H_{34}ClN_3O_3S$ (540.12) Calculated: C, 64.48; H, 6.34; N, 7.78. Found: C, 64.42; H, 6.60; N, 7.52.

The following compound is obtained analogously:

6-(4-(2-(4-chlorobenzenesulphonylamino)ethyl)-phenyl)-6-(3-pyridyl)hex-5-enoic acid benzylamide Yield: 51% of theory.

Resin, $R_f$ value: 0.37 (silica gel: ethyl acetate).

$C_{32}H_{32}ClN_3O_3S$ (574.14). Calculated: C.66.94; H, 5.61; N, 7.31. Found: C, 66.72; H, 5.44; N, 7.10.

EXAMPLE 28

6-(4-(2-(N-Methyl-4-chlorobenzenesulphonylamino)ethyl)phenyl)-6-(3-pyridyl)hex-5-enoic acid 2.0 g of 6-(4-(2-(4-chlorobenzenesulphonylamino)ethyl)-phenyl)-6-(3-pyridyl)hex-5-enoic acid are stirred overnight in 10 ml of 4N sodium hydroxide solution, 100 ml of methylene chloride, 80 mg of benzyl trimethylammonium chloride and 0.85 g of methyl iodide. Then the organic phase is separated off and the aqueous phase is acidified to pH 5. The product precipitated is separated off and taken up in methylene chloride, dried and evaporated down. Finally, the residue is chromatographed with ethylene chloride/methanol (97:3) over a silica gel column.

Yield: 0.43 g (21% of theory).

Melting point: 121°–125° C.

$C_{26}H_{27}ClN_2O_4S$ (499.02): Calculated: C, 62.58; H, 5.45; N, 5.61. Found: C, 62.53; H, 5.54; N, 5.53.

EXAMPLE 29

6-(4-(2-(4-Chlorobenzenesulphonylamino)ethyl)-phenyl)-6-(3-pyridyl)-2,2-dimethyl-hex-5-enoic acid a)

6-(4-(2-(4-Chlorobenzenesulphonylamino)ethyl)-phenyl)-6-(3-pyridyl)-2,2-dimethyl-hex-5-enoic acid piperidide Prepared analogously to Example 7d from 4-triphenylphosphonium butanoic acid piperidide bromide and 4-(2-(4-chlorobenzenesulphonylamino)ethyl)phenyl-3-pyridyl ketone.

Yield: 6.7% of theory.

Resin, $R_f$ value: 0.4 (silica gel: ethyl acetate), $C_{32}H_{38}ClN_3O_3S$ (580.16): Calculated: C, 66.24; H, 6.60; N, 7.24. Found: C, 66.15; H, 6.33; N, 7.11.

b)

6-(4-(2-(4-Chlorobenzenesulphonylamino)ethyl)-phenyl)-6-(3-pyridyl)-2.2-dimethyl-hex-5-enoic acid 0.35 g of 6-(4-(2-(4-chlorobenzenesulphonylamino)ethyl)phenyl)-6-(3-pyridyl)-2,2-dimethyl-hex-5-enoic acid piperidide are refluxed for 8 hours in 20 ml of 6N hydrochloric acid. Then the mixture is evaporated down and the residue is dissolved in sodium hydroxide solution and adjusted to pH 4 using hydrochloric acid. The precipitate formed is suction filtered and chromatographed over a silica gel column using ethylene chloride/methanol (10:1).

Yield: 0.12 g (39% of theory).

Resin, $R_f$ value: 0.5 (silica gel: ethylene chloride/methanol=9:1).

$C_{27}H_{29}ClN_2O_4S$ (513.04); Calculated: C, 63.21; H, 5.70; N, 5.46. Found: C, 63.08; H, 5.58; N, 5.60.

EXAMPLE 30

6-(4-(2-(2,4,6-Trimethylbenzenesulphonylamino)ethyl)-phenyl)-6-(3-pyridyl)hex-5-enoic acid a) Methyl 6-(4-(2-aminoethyl)phenyl)-6-(3-pyridyl)hex-5-enoate

Prepared by hydrolysis of 6-(4-(2-acetylaminoethyl)-phenyl)-6-(3-pyridyl)hex-5-enoic acid and subsequent esterification with methanol analogously to Example 8b.

Yield: 87% of theory.

Resin, $R_f$ value: 0.6 (silica gel: dioxan/toluene/methanol/ammonia=5:2:2:1), $C_{20}H_{24}N_2O_2$ (324.42): Calculated: C, 74.05; H, 7.46; N, 8.63, Found: C, 73 85; H, 7.58; N, 8.52, b)

6-(4-(2-(2,4,6-Trimethylbenzenesulphonylamino)ethyl)-phenyl)-6-(3-pyridyl)hex-5-enoic acid A mixture of 3.24 g of methyl 6-(4-(2-aminoethyl)-phenyl)-6-(3-pyridyl)hex-5-enoate, 2.2 g of 2,4,6-trimethylbenzenesulphonic acid chloride and 100 ml of triethylamine in 50 ml of dichloromethane is stirred for 30 minutes at ambient temperature. Then the reaction mixture is washed twice with water, dried and evaporated down. The residue is purified over a silica gel column using ethyl acetate. The crude product obtain is heated in a mixture of 32 ml of ethanol and 5 ml of 4N sodium hydroxide solution for 30 minutes to 50° to 60° C. The reaction mixture is evaporated down, the residue is taken up in 50 ml of water and washed with ethyl acetate. The aqueous phase is adjusted to pH 5 by the addition of citric acid and extracted twice with ethyl acetate. The organic phase is dried, evaporated down and the residue is chromatographed over a silica gel column using ethyl acetate. The crude product is then recrystallised from ethyl acetate/diisopropyl ether.

Yield: 1.35 g (28% of theory).
Melting point: 79°-83° C.
$C_{28}H_{32}N_2O_4S$ (492.64):
Calculated: C, 68.27; H, 6.55; N, 5.68, Found: C, 68.00; H, 6.51; N, 5.68, The following compounds are obtained analogously:
6-(4-(2-(2,3,5,6-tetramethylbenzenesulphonylamino)ethyl)phenyl)-6-(3-pyridyl)hex-5-enoic acid
Melting point: 135°-136° C.
$C_{29}H_{34}N_2O_4S$ (506.67): Calculated: C, 68.75; H, 6.76, N, 5.33. Found: C, 68.91; H, 6.81, N, 5.37.

6-(4-(2-(2,3,4,5,6-pentamethylbenzenesulphonylamino)ethyl)phenyl)-6-(3-pyridyl)hex-5-enoic acid
Melting point: 158°-160° C. (ethyl acetate/diethyl ether).
$C_{30}H_{36}N_2O_4S$ (520.69): Calculated: C, 69.20; H, 6.97; N, 5.38. Found: C, 69.00; H, 7.14; N, 5.49.

6-(4-(2-(4-methoxybenzenesulphonylamino)ethyl)phenyl)-6-(3-pyridyl)hex-5-enoic acid
Melting point: 104°-106° C.
$C_{26}H_{28}N_2O_5S$ (480.58): Calculated: C, 64.9; H, 5.87; N, 5.83. Found: C, 64.90; H, 6.02; N, 5.99.

6-(4-(2-(3,4-dimethoxybenzenesulphonylamino)ethyl)phenyl)-6-(3-pyridyl)hex-5-enoic acid
Yield: 18% of theory.
Resin, $R_f$ value: 0.36 (silica gel: dichloromethane/ethyl acetate=6:4+3% acetic acid),
$C_{27}H_{30}N_2O_6S$ (510.61): Calculated: C, 63.51; H, 5.92; N, 5.49. Found: C, 63.21; H, 5.79; N, 5.33.

6-(4-(2-(4-trifluoromethylbenzenesulphonylamino)ethyl)phenyl)-6-(3-pyridyl)hex-5-enoic acid
Melting point: 140°-143° C. (ethyl acetate/petroleum ether).
$C_{26}H_{25}F_3N_2O_4S$ (518.56): Calculated: C, 60.22; H, 4.86; N, 5.40.Found C, 60.05; H, 4.77; N, 5.66.

6-(4-(2-(5-chlorothiophene-2-sulphonylamino)ethyl)phenyl)-6-(3-pyridyl)hex-5-enoic acid
Melting point: 113°-115° C.
$C_{23}H_{23}ClN_2O_4S_2$ (491.03): Calculated: C, 56.26; H, 4.72; N, 5.70. Found: C, 55.96; H, 4.70; N, 5.79.

6-(4-(2-(phenylmethanesulphonylamino)ethyl)phenyl)-6-(3-pyridyl)hex-5-enoic acid
$C_{26}H_{28}N_2O_4S$ (464.58):
Resin, $R_f$ value: 0.64 (silica gel: ethyl acetate). Calculated: C, 67.22; H, 6.07; N, 6.03, Found: C, 67.27; H, 6.22; N, 5.88.

EXAMPLE 31

E- and Z-6-(4-(2-(4-Chlorobenzenesulphonylamino)ethyl)-phenyl)-6-(3-pyridyl)hex-5-enoic acid a)

4-(2-(4-Chlorobenzenesulphonylamino)ethyl)phenyl-3-pyridyl ketone 156 g of 4-(2-acetylaminoethyl)phenyl-3-pyridyl ketone are heated for 16 hours in 800 ml of 6N hydrochloric acid. The solution is evaporated down and the residue is taken up in a mixture of 200 ml of water and 500 ml of dioxan. By the addition of 10N sodium hydroxide solution a pH of 8 to 10 is established. Then a solution of 126 g of 4-chlorobenzenesulphonic acid chloride in 150 ml of dioxan and 10N sodium hydroxide solution is added dropwise at ambient temperature so as to maintain a pH of 8 to 10. The reaction mixture is added to a mixture of 1 kg of ice and 400 ml of toluene and the precipitate is suction filtered. The crude product precipitated is recrystallised from toluene.

Yield: 148 g (65% of theory).
Melting point: 159°-160° C.
$C_{20}H_{17}ClN_2O_3S$ (400.91): Calculated: C, 59.92; H, 4.28; N, 6.99. Found: C, 60.00; H, 4.10; N, 6.91.

b)

E-6-(4-(2-(4-Chlorobenzenesulphonylamino)ethyl)-phenyl)-6-(3-pyridyl)hex-5-enoic acid 222 g of 4-carboxybutyl-triphenylphosphonium bromide are suspended in 2000 ml of tetrahydrofuran and cooled to <20° C. To this suspension are added 156 g of potassium tert.butoxide followed by 155 g of 4-(2-(4-chlorobenzenesulphonylamino)ethyl)phenyl)-3-pyridyl ketone. The mixture is stirred for 1.5 hours whilst the temperature is allowed to rise to 10° C. The reaction mixture is poured onto 5000 ml of ice water. The aqueous phase is washed with ethyl acetate and then adjusted to pH 5 by the addition of citric acid. The precipitate is suction filtered and recrystallised from water/ethanol.

Yield: 140 g (75% of theory),
Melting point: 159°-160° C.
$C_{25}H_{25}ClN_2O_4S$ (485.00): Calculated: C, 61.91; H, 5.20; N, 5.78. Found: C, 61.67; H, 5.06; N, 5.70.

c)

Z-6-(4-(2-(4-Chlorobenzenesulphonylamino)ethyl)-phenyl)-6-(3-pyridyl)hex-5-enoic acid The mother liquor from Example 31b is evaporated down and extracted with ethyl acetate. The organic extract is evaporated down and the residue is chromatographed over a silica gel column with (ethylene chloride/ethyl acetate=6:4+3% acetic acid). The faster running fraction is collected, evaporated down and the residue is recrystallised from ethyl acetate/diethyl ether.

Yield: 7.8 g (3% of theory).
Melting point: 94°-95° C.
$C_{25}H_{25}ClN_2O_4S$ (485.00): Calculated: C, 61.91; H, 5.20; N, 5.78. Found: C, 61.66; H, 5.23; N, 5.87.

EXAMPLE 32

6-(2-(4-Chlorobenzenesulfonylamino)-1,2,3,4-tetrahydronaphth-6-yl)-6-(3-pyridyl)hex-5-enoic acid a) 2-Amino-6-bromo-1,2,3,4-tetrahydronaphthaline hydrochloride 55.8 g of titanium tetrachloride were dropped cautiously to 700 ml of ethylene glycol dimethylether at 0° C. Subsequently 22.3 g of sodium boron hydride and then a solution of 33.5 g of 6-bromo-2-oximino-1,2,3,4-tetrahydronaphthaline were added to the reaction mixture. After stirring for four hours, the mixture was poured on ice, made alkaline with concentrated ammonia and filtrated over kieselguhr. The filtrate was extracted with methylene chloride and evaporated in vacuum. The obtained residue was dissolved in ether and the hydrochloride was precipitated by addition of isopropanolic hydrochloric acid.

Yield: 20,2 g (55 % of theory).
Melting Point: 237° C.
$C_{10}H_{12}Brn \times HCl$ (262,5): Calculated: C, 45,74; H, 4,99; N, 5,33. Found: C, 45,9; H, 5,22; N, 5,24.

b) 2-tert.Butoxycarbontlamino-6-bromo-1,2,3,4-tetrahydronaphthaline 44 ml of 1N sodium hydroxide and subsequently 4,8 g of di-tert.butyl dicarbonate were added to a solution of 5.25 g of 2-amino-6-bromo-1,2,3,4-tetrahydronaphthaline in 75 ml of dioxane/water (2:1) at 0° C. After stirring for 12 hours at room temperature, the mixture was evaporated, mixed with water and extracted with ethyl acetate. The organic phase was evaporated and the residue obtained recrystallised from petroleum ether.

Yield: 5,2 g (80% of theory).
Melting point 111° C.
$C_{15}H_{20}BrNO_2$ (326,23): Calculated: C, 55,23; H, 6,18; N, 4,29, Found: C, 55,08, H, 6,29; N, 4,51, c) 2-tert.Butoxycarbonylamino-6-bromo-1,2,3,4-tetrahydronaphth-6-yl-3-pyridylmethanol 8.8 ml of a solution of n-butyl lithium in hexane (2.5 mol) was dropped to a solution of 3.25 g of 2-tert.butoxycarbonylamino-6-bromo-1,2,3,4-tetrahydro-naphthaline in 50 ml of absolute tetrahydrofurane cooled to −70° C. and stirring was continued for 1.5 hours at −50° C. Subsequently, 1.1 g of pyridine-3-aldehyde were dropped into the mixture at −70° C. After stirring for one hour, the reaction mixture was poured on ice and extracted with ethyl acetate. The organic Phase was washed with water, dried and evaporated. The obtained residue was recrystallised from cyclohexane/ethyl acetate.

Yield: 1,85 g (52% of theory).
Melting point 135° C.
$C_{21}H_{26}N_2O_3$ (354.45), Calculated: C, 71.16; H, 7.39; N, 7.90. Found: C, 70,96; H, 7,46; N, 7,86.

d) 2-(4-Chorobenzenesulfonylamino)-1,2,3,4-tetrahydronaphth-6-yl-3-pyridyl ketone 1,75 g of 2-tert.butoxycarbonylamino-1,2,3,4-tetrahydronaphth-6-yl-3-pyridyl methanol were stirred in 30 ml of chloroform with 17,5 g of manganese dioxide for one hour at room temperature. After filtering the suspension, the filtrate was evaporated and the obtained residue was stirred in 10 ml of 2N hydrochloric acid for one hour at 40°–50° C. The reaction mixture was made alkaline by addition of concentrated ammonia and extracted with ethyl acetate. The organic phase was washed with water and evaporated. 0.86 g of 4-chlorobenzenesulphonic acid chloride and additionally 1 g of triethylamine were added to a solution of the obtained residue in 20 ml of methylene chloride at 0° C. After stirring for two hours, the reaction mixture was poured on ice and extracted with methylene chloride. The organic phase was washed with water, dried and evaporated. The obtained residue was recrystallised from ethyl acetate/petroleum ether.

Yield: 1,2 g (57% of theory).
Melting point: 170°–172° C.
$C_{22}H_{19}ClN_2O_3S$ (426,92): Calculated: C, 61,89; H, 4,49 N, 6,56. Found: C, 61,63; H, 4,62 N, 6,39.

e) 6-(2-(4-Chlorobenzenesulfonylamino)-1,2,3,4-tetrahydronaphth-6-yl)-6-(3-pyridyl)hex-5-enoic acid Prepared from 2-(4-chlorobenzenesulfonylamino)-1,2,3,4-tetrahydronaphth-6-yl-3-pyridyl ketone and 4-carboxybutyl-triphenylphosphonium bromide analogously to Example 31b.

Yield: 63% of theory.
Melting Point: 172° C.
$C_{27}H_{27}ClN_2O_4S$: Calculated: C, 63,46; H, 5,33; N, 5,48. Found: C, 63,42; H, 5,41; N, 5,43,

EXAMPLE I

Tablets containing 100 mg of 6-(4-(2-(4-chlorobenzenesulphonylamino)ethyl)-phenyl)-6-(3-pyridyl)hex-3-enoic acid

| Composition: 1 tablet contains: | |
|---|---|
| Active substance | 100.0 mg |
| Lactose | 80.0 mg |
| Corn starch | 34.0 mg |
| Polyvinylpyrrolidone | 4.0 mg |
| Magnesium stearate | 2.0 mg |
| | 220.0 mg |

Preparation process

The active substance, lactose and starch are mixed together and uniformly moistened with an aqueous solution of the polyvinylpyrrolidone. After the moist masses have been screened (2.0 mm mesh size) and dried in a rack dryer at 50° C. they are screened again (1.5 mm mesh) and the lubricant is added. The mixture produced is formed into tablets.

| Weight of tablet: | 220 mg |
|---|---|
| Diameter: | 9 mm, biplanar, facetted on both sides and notched on one side. |

EXAMPLE II

Hard gelatin capsules containing 150 mg of 6-(4-(2-(4-chlorobenzenesulphonylamino)ethyl)-phenyl)-6-(3-pyridyl)hex-3-enoic acid

| 1 capsule contains: | |
|---|---|
| Active substance | 150.0 mg |

-continued

| 1 capsule contains: | | |
|---|---|---|
| Dried corn starch | about | 180.0 mg |
| Dried lactose | about | 87.0 mg |
| Magnesium stearate | | 3.0 mg |
| | about | 320.0 mg |

Preparation

The active substance is mixed with the excipients, passed through a 0.75 mm mesh screen and homogeneously mixed in a suitable apparatus. The final mixture is packed into size 1 hard gelatin capsules.

Capsule contents: about 320 mg
Capsule shell: size 1 hard gelatin capsule.

Example III

Suppositories containing 150 mg of 6-(4-(2-(4-chlorobenzenesulphonylamino)ethyl)-phenyl)-6-(3-pyridyl)hex-3-enoic acid

| 1 suppository contains: | |
|---|---|
| Active substance | 150.0 mg |
| Polyethyleneglycol (M.W. 1500) | 550.0 mg |
| Polyethyleneglycol (M.W. 6000) | 460.0 mg |
| Polyoxy polyoxy ethylene sorbitan monostearate | 840.0 mg |
| | 2000.0 mg |

Preparation

After the suppository masses have been melted the active substance is homogeneously distributed therein and the melt is poured into chilled moulds.

EXAMPLE IV

Suspensions containing 50 mg of 6-(4-(2-(4-chlorobenzene-sulphonylamino)ethyl)-phenyl)-6-(3-pyridyl)hex-3-enoic acid

| 100 ml of suspension contain: | | |
|---|---|---|
| Active substance | | 1.0 g |
| Sodium salt of carboxymethylcellulose | | 0.2 g |
| Methyl p-hydroxybenzoate | | 0.05 g |
| Propyl p-hydroxybenzoate | | 0.01 g |
| Glycerol | | 5.0 g |
| 70% Sorbitol solution | | 50.0 g |
| Flavouring | | 0.3 g |
| Distilled water | ad | 100 ml |

Preparation

Distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the addition of the sorbitol solution and flavouring, the suspension is evacuated to eliminate air, with stirring. 5 ml of suspension contain 50 mg of active substance.

EXAMPLE V

Tablets containing 150 mg of 6-(4-(2-(4-chlorobenzenesulphonylamino)ethyl)-phenyl)-6-(3-pyridyl)hex-5-enoic acid

| Composition: 1 tablet contains: | |
|---|---|
| Active substance | 150.0 mg |
| Powdered lactose | 89.0 mg |
| Corn starch | 40.0 mg |
| Colloidal silica | 10.0 mg |
| Polyvinylpyrrolidone | 10.0 mg |
| Magnesium stearate | 1.0 mg |
| | 300.0 mg |

Preparation

The active substance mixed with lactose, corn starch and silica is moistened with a 20% aqueous polyvinylpyrrolidone solution and passed through a 1.5 mm mesh screen. The granules dried at 45° C. are rubbed through the same screen again and mixed with the specified amount of magnesium stearate. Tablets are compressed from the mixture.

Weight of tablet: 300 mg
Punch: 10 mm, flat

EXAMPLE VI

Film-coated tablets containing 75 mg of 6-(4-(2-(4-chlorobenzenesulphonylamino)ethyl)-phenyl)-6-(3-pyridyl)hex-5-enoic acid

| 1 tablet core contains: | |
|---|---|
| Active substance | 75.0 mg |
| Calcium phosphate | 93.0 mg |
| Corn starch | 35.5 mg |
| Polyvinylpyrrolidone | 10.0 mg |
| Hydroxypropylmethylcellulose | 15.0 mg |
| Magnesium stearate | 1.5 mg |
| | 230.0 mg |

Preparation

The active substance is mixed with calcium phosphate, corn starch, polyvinylpyrrolidone, hydroxypropylmethylcellulose and half the specified amount of magnesium stearate. Using a tablet making machine, compressed tablets are produced about 13 mm in diameter which are then rubbed through a 1.5 mm mesh screen on a suitable machine and mixed with the remaining magnesium stearate. These granules are compressed in a tablet making machine to form tablets of the desired shape.

Weight of core: 230 mg
Punch: 9 mm, convex

The tablet cores thus produced are coated with a film consisting essentially of hydroxypropylmethylcellulose. The finished film coated tablets are glazed with beeswax.

Weight of film coated tablet: 245 mg

Obviously all the other compounds of general formula I may be used as active substances in the galenic preparations described above.

EXAMPLE VII

Film coated tablets containing 75 mg of 6-(4-(2-(4-chlorobenzenesulphonylamino)ethyl)-phenyl)-6-(3-pyridyl)hex-5-enoic acid (Substance B) +75 mg of PDE inhibitor

| A powder mixture of | |
|---|---|
| Dipyridamole | 25% |
| Substance B | 25% |
| Fumaric acid | 15% |
| Cellulose | 20% |
| Corn starch | 8% |
| Polyvinylpyrrolidone | 6% | is moistened with water in a mixing apparatus and granulated through a screen with a mesh size of 1.5 mm. After drying and screening again, 1% magnesium stearate is added and 10 mm biconvex tablets are produced weighing 300 mg. These tablets are sprayed with hydroxypropylmethylcellulose lacquer until they weigh 312 mg.

EXAMPLE VIII

Hard gelatin capsules containing 200 mg of 6-(4-(2-(4-chlorobenzenesulphonylamino)ethyl)-phenyl)-6-(3-pyridyl)-hex-5-enoic acid (Substance B)+50 mg of PDE inhibitor 10 kg of dipyridamole, 20 kg of fumaric acid, 11.5 kg of polyvinylpyrrolidone, 40 kg of substance B, 1.5 kg of silicon dioxide and 0.8 kg of magnesium stearate are mixed for 15 minutes in a cube mixer. This mixture is fed into a roller compactor followed by a dry granulating apparatus with screening device. The fraction from 0.25 to 1.0 mm is used. The capsule filling machine is set so that each size 0 capsule contains the quantity of granules corresponding to 50 mg of PDE inhibitor and 200 mg of substance B.

EXAMPLE IX

Hard gelatin capsules containing 100 mg of 6-(4-(2-(4-chlorobenzenesulphonylamino)ethyl)-phenyl)-6-(3-pyridyl)hex-5-enoic acid (Substance B) +250 mg of PDE inhibitor a) Granules 125 kg of mopidamole, 50 kg of fumaric acid and 13.5 kg of lactose are mixed together and moistened with a solution of water/polyethyleneglycol 6000. After granulation through a screen with a mesh size of 1.0 mm and drying at 45° C., 1.4 kg of stearic acid are added.

b) Coated tablet 100 kg of substance B, 7.5 kg of hydroxypropylmethylcellulose, 2.5 kg of silicon dioxide and 15 kg of carboxymethylcellulose are moistened with ethanol and granulated through a screen with a mesh size of 1.5 mm. After drying, 1 kg of magnesium stearate is added and the granules are compressed to form biconvex tablets weighing 126 mg and having a diameter of 5.5 mm.

These cores are coated in several steps with a coating suspension consisting of 5.6 kg of saccharose, 0.5 kg of gum arabic and 3.8 kg of talc until the tablets weight 135 mg.

c) Filling

In a special capsule making machine, hard gelatin capsules of size 0 long are packed with a quantity of granules corresponding to 250 mg of PDE inhibitor and the coated tablet containing 100 mg of substance B is placed on top.

EXAMPLE X

Suspension containing 10 mg of 6-(4-(2-(4-chlorobenzenesulphonylamino)ethyl)phenyl)-6-(3-pyridyl)hex-5-enoic acid (Substance B)+100 mg of dipyridamole per 5 g The suspension has the following composition:

| (1) Dipyridamole | 2.0% |
|---|---|
| (2) Substance B | 0.2% |
| (3) Sorbitol | 20.8% |
| (4) Cellulose | 7.5% |
| (5) Sodium carboxymethylcellulose | 2.5% |
| (6) Flavour correctors/preservatives | 1.8% |
| (7) Water | 65.2% |

Ingredients (3) to (6) are stirred into hot water under high shear forces. After cooling, ingredients (1), (2) and (7) are incorporated in the viscous suspension.

EXAMPLE XI

Delayed release form containing 50 mg of 6-(4-(2-(4-chlorobenzenesulphonylamino)ethyl)-phenyl)-6-(3-pyridyl)hex-5-enoic acid (Substance B)+200 mg of dipyridamole a) Pellet I

| A mixture of | |
|---|---|
| Substance B | 50.0 kg |
| Lysine | 12.5 kg |
| High polymeric hydroxypropylcellulose | 52.5 kg |
| Triacetin | 4.0 kg |
| Ethylcellulose | 2.5 kg |
| Magnesium stearate | 3.5 kg | is kneaded with ethanol in a special extruder and extruded in the form of spaghetti (diameter 1 mm) which is formed into pellets in a spheronizer. These pellets are then thoroughly dried.

b) Pellet II 300 kg of tartaric acid starter pellets are sprayed, in a special container, with a suspension of isopropanol, dipyridamole and polyvinylpyrrolidone until the active substance pellets produced contain about 45% of dipyridamole.

These pellets are sprayed with a lacquer consisting of methacrylic acid/methylmethacrylate copolymer (sold under the name Eudragit S) and hydroxymethylcellulose phthalate (sold under the name HP 55) in a weight ratio of 85:15 to 50:50. The organic lacquer solution also contain plasticiser and talc. Two pellet components are sprayed with 5 and 7% of coating composition and different ratios of lacquer components within the limits specified. The two components are mixed together to give the following in vitro release:

Conditions (corresponding to USPXXI, Basket method, 100 rpm,

1st hour in artificial gastric juice, pH 1.2, 2nd to 6th hours in artificial intestinal juice (phosphate buffer), pH 5.5):

Release of active substance per hour:

| 1st hour | about 30% |
|---|---|
| 2nd hour | about 25% |
| 3rd hour | about 18% |

| | |
|---|---|
| 4th hour | about 12% | after the 6th hour more than 90% of dipyridamole is released.

c) Filling

The pellets are mixed together in accordance with the content of active substance of pellet components I and II and the required dose and packed into size 0 long capsules in a capsule filling machine.

EXAMPLE XII

Ampoules containing 5 mg of 6-(4-(2-(4-chlorobenzenesulphonylamino)ethyl)-phenyl)-6-(3-pyridyl)hex-5-enoic acid (Substance B)+10 mg of dipyridamole per 5 ml

| Composition: | | |
|---|---|---|
| (1) Dipyridamole | | 10 mg |
| (2) Substance B | | 5 mg |
| (3) Propyleneglycol | | 50 mg |
| (4) Polyethyleneglycol | | 5 mg |
| (5) Ethanol | | 10 mg |
| (6) Water for injections | ad | 5 ml |
| (7) Dilute HCl | ad | pH 3 |

The active substances are dissolved, with heating, in the solution consisting of ingredients (3) to (7). After checking the pH and sterilising by filtration the solution is transferred into suitable ampoules and sterilised.

What is claimed is:

1. Arylsulphonamides of formula $$R_1-SO_2-N(R_2)-A-C(R_3)(R_4)-CH(R_5)-B-CO-R_6 \quad (I)$$

wherein
R$_1$ is a phenylalkyl, trialklphenyl, tetramethylphenyl or pentamethylphenyl group, a thienyl group optionally substituted by a halogen atom or an alkyl group, or a phenyl group which may be mono-substituted by a nitro group or mono- or disubstituted by a halogen atom or by an alkyl, trifluoromethyl or alkoxy group, the substituents being identical or different, R$_2$, R$_4$ and R$_5$, which may be identical or different, are hydrogen or alkyl or R$_2$ is a hydrogen atom or an alkyl group and R$_4$ and R$_5$ together represent a carbon-carbon bond, R$_3$ is a 2-, 3- or 4- pyridyl group optionally substituted by an alkyl group, R$_6$ is a hydroxy, alkoxy, amino, alkylamino or dialkylamino group, A is a group of formula

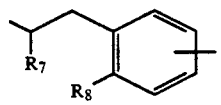

wherein
R$_7$ and R$_8$ together are a methylene or ethylene group, and

B is a carbon-carbon bond or a straight-chained C$_1$-C$_4$ alkylene group optionally substituted by one or two alkyl groups, the alkyl and alkoxy moieties may each contain 1 to 3 carbon atoms,
the enantiomers thereof, the cis and trans isomers thereof, where R$_4$ and R$_5$ together represent a carbon-carbon bond, and the pharmaceutically acceptable addition salts thereof.

2. The arylsulphonamides as recited in claim 1 wherein
R$_1$ is a benzyl, thienyl, chlorothienyl, dichlorophenyl, dimethoxyphenyl, tetramethylphenyl or pentamethylphenyl group or a phenyl group optionally substituted by a fluorine or chlorine atom or by a nitro, methyl or trifluoromethyl group, R$_2$, R$_4$ and R$_5$ each are hydrogen or methyl or R$_2$ is a hydrogen atom or a methyl group and R$_4$ and R$_5$ together are a carbon-carbon bond, R$_3$ is a 2-, 3- or 4- pyridyl group, R$_6$ is a hydroxy or methoxy group, A represents a group of formula

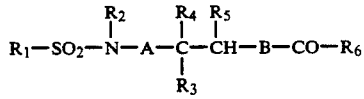

wherein
R$_7$ and R$_8$ together are a methylene or ethylene group and

B is a carbon-carbon bond or a straight-chained C$_{2-4}$ alkylene group,
the enantiomers thereof, the cis and trans isomers thereof where R$_4$ ad R$_5$ together represent a carbon-carbon bond, and the pharmaceutically acceptable addition salts thereof.

3. The arylsulphonamides as recited in claim 1 wherein
R$_1$ is a tetramethylphenyl or pentamethylphenyl group or a phenyl group substituted in the 4-position by a methyl or trifluoromethyl group or by a fluorine, chlorine or bromine atom, R$_2$, R$_4$ and R$_5$ each are hydrogen or R$_2$ is hydrogen and R$_4$ an R$_5$ together are a carbon-carbon bond, R$_3$ is a 3-pyridyl group, A is a group of the formula

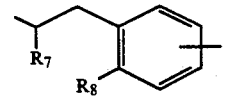

wherein
R$_7$ and R$_8$ together are a methylene group,

R$_6$ is a hydroxy group and

B is a straight-chained C$_{2-4}$ alkylene group,
the enantiomers thereof, the cis and trans isomers thereof where R$_4$ and R$_5$ together are a carbon-carbon bond, and the pharmaceutically acceptable addition salts thereof.

4. 6-[2-(4-toluenesulphonylamino)indan-5-yl]-6-(3-pyridyl)-hex-5-enoic acid and the addition salts thereof.

5. A pharmaceutical composition comprising an arylsulphonamide as recited in claim 1 and a pharmaceutically acceptable carrier.

6. The pharmaceutical composition as recited in claim 5 further comprising a PDE inhibitor.

7. The pharmaceutical composition as recited in claim 5 further comprising a lysing agent.

* * * * *